US006407237B1

(12) United States Patent
Glasky et al.

(10) Patent No.: US 6,407,237 B1
(45) Date of Patent: Jun. 18, 2002

(54) CRYSTAL FORMS OF 9-SUBSTITUTED HYPOXANTHINE DERIVATIVES

(75) Inventors: Alvin J. Glasky, Tustin, CA (US); Heinrich Bollinger, Beringen; Hans Rudolf Müller, Schaffhausen, both of (CH)

(73) Assignee: NeoTherapeutics, Inc., Irvine, CA (US)

( * ) Notice: Subject to any disclaimer, the term of this patent is extended or adjusted under 35 U.S.C. 154(b) by 0 days.

(21) Appl. No.: 09/505,984

(22) Filed: Feb. 16, 2000

(51) Int. Cl.$^7$ .............................................. C07D 473/30
(52) U.S. Cl. ..................................................... 544/265
(58) Field of Search ........................................ 544/265

(56) References Cited

U.S. PATENT DOCUMENTS

| | | | |
|---|---|---|---|
| 3,300,380 A | 1/1967 | Gray et al. ................... 167/65 |
| 3,321,369 A | 5/1967 | Glasky et al. ................. 167/65 |
| 3,438,968 A | 4/1969 | Glasky et al. ............ 260/211.5 |
| 3,666,856 A | 5/1972 | Elion et al. .................. 424/180 |
| 4,035,486 A | 7/1977 | Laborit ........................ 424/128 |
| 4,138,562 A | 2/1979 | Vince .......................... 544/326 |
| 4,221,794 A | 9/1980 | Simon et al. ................. 544/265 |
| 4,221,909 A | 9/1980 | Simon et al. ................. 544/265 |
| 4,221,910 A | 9/1980 | Giner-Sorolla .............. 544/265 |
| 4,315,920 A | 2/1982 | Schaeffer et al. ............. 424/10 |
| 4,340,726 A | 7/1982 | Simon et al. ................. 544/265 |
| 4,347,360 A | 8/1982 | Ogilvie ........................ 544/276 |
| 4,451,478 A | 5/1984 | Simon et al. ................. 544/276 |
| 4,643,992 A | 2/1987 | Goodman et al. ............. 514/45 |
| 4,952,693 A | 8/1990 | Sircar et al. ................. 544/276 |
| 5,023,294 A | 6/1991 | Goto et al. .................... 514/46 |
| 5,091,432 A | 2/1992 | Glasky ........................ 544/265 |
| 5,093,318 A | 3/1992 | Goodman et al. ............. 514/45 |
| 5,187,162 A | 2/1993 | Marangos et al. ............. 514/46 |
| 5,237,051 A | 8/1993 | Garbers et al. .............. 530/350 |
| 5,256,677 A | 10/1993 | Sham et al. ................. 514/351 |
| 5,376,642 A | 12/1994 | Yarchoan et al. ............. 514/45 |
| 5,447,939 A | 9/1995 | Glasky ........................ 514/310 |
| 5,565,437 A | 10/1996 | Marquez et al. ............... 514/45 |
| 5,595,901 A | 1/1997 | Rocancourt et al. ........ 435/232 |
| 5,795,756 A | 8/1998 | Johnson et al. ............. 435/183 |
| 5,801,159 A | 9/1998 | Miller et al. ................. 514/45 |
| 5,801,184 A | 9/1998 | Glasky ........................ 544/265 |
| 5,948,771 A | 9/1999 | Danziger .................... 514/185 |
| 6,027,936 A | 2/2000 | Glasky ........................ 514/310 |

FOREIGN PATENT DOCUMENTS

| WO | WO 99/56550 | 11/1999 |
| WO | WO 99/57119 | 11/1999 |
| WO | WO 99/57120 | 11/1999 |

OTHER PUBLICATIONS

N.W. Tietz, ed., "Textbook of Clinical Chemistry" (W.B. Sauders Co., Philadelphia, 1986), pp. 882–886.

G.A. Lyles & B.A. Callingham, "The Effects of Thyroid Hormones on Monoamine Oxidase in the Rat Heart," *J. Pharm. Pharmacol.* 26:921–930 (1974).

S.K. Gupta & R.K. Mishra, "Desensitization of $D_1$ Dopamine Receptors Down–Regulates the $G_s\alpha$ Subunit of G Protein in SK–N–MC Neuroblastoma Cells," *J. Mol. Neurosci.* 4:117–123 (1993).

(List continued on next page.)

*Primary Examiner*—Mark L. Berch
(74) *Attorney, Agent, or Firm*—Oppenheimer Wolff & Donnelly LLP

(57) ABSTRACT

The bifunctional compound N-4-carboxyphenyl-3-(6-oxohydropurin-9-yl) propanamide monopotassium salt occurs in a number of crystal forms which differ in their stability. Of these forms, the most stable is designated Type I, which is a monopotassium salt monohydrate in which the water is held as water of crystallization. Other crystalline forms, designated Type II and Type III, convert to Type I. Methods are disclosed for the synthesis of Type I and for the conversion of Type II or Type III to Type I.

6 Claims, 19 Drawing Sheets

OTHER PUBLICATIONS

S.K. Gupta & R.K. Mishra, "Up–Regulation of $D_1$ Dopamine Receptors in SK–N–MC Cells After Chronic Treatment with SCH 23390," Neurosci. Res. Commun. 15:157–166 (1994).

P.W. Bauers et al., "Design, Synthesis, X–Ray Analysis, and Dopamine Receptor–Modulating Activity of Mimics of the 'C5' Hydrogen–Bonded Conformation in the Peptidomimetic 2–Oxo–3–(R)–[(2(S)–Pyrrolidinylcarbonyl)-amino]–1–Pyrrolidineacetamide," J. Med. Chem. 37: 3677–3683 (1994).

J.E. Savelli et al., "Modulation of N–Methyl–D–Aspartate (NMDA) Antagonist–Induced Darting Behaviour by the Peptidomimetic PAMTA," Brain Res. 682: 41–49 (1995).

K.A. Jacobson, "Chemical Approaches to the Definition of Adenosine Receptors" in Adenosine Receptors (D.M.F. Cooper & C. Londos, eds., Receptor Biochemistry and Methodology, J.C. Venter, L.C. Harrison, eds., Alan R. Liss: New York, 1988), pp. 11:1–26.

S.H. Appel & J.L. McManaman, "Is a Breakdown of the Blood–Brain Barrier Cause or Effect?, " Neurobiol. Aging 7:512–514 (1986).

S.M. MacDonald et al., "Immunological Parameters in the Aged and in Alzheimer's Disease," Clin. Exp. Immunol. 49:123–128 (1982).

A.E. Miller et al., "Immunological Studies in Senile Dementia of the Alzheimer Type: Evidence for Enhanced Suppressor Cell Activity," Ann. Neurol. 10:506–510 (1981).

K. Stefansson, "Neuroimmunology of Aging" in Clinical Neurology of Aging (M.L. Albert, ed., Oxford University Press, Oxford, (1984)), ch. 4, pp. 76–94.

L.R. Weitkamp et al., "Alzheimer Disease: Evidence for Susceptibility Loci on Chromosomes 6 and 14," Am. J. Hum. Genet. 35:443–53 (1983).

A. Yamazaki et al., Synthesis of Guanosine and Its Derivatives from 5–Amino–1–β–D–Ribofuranosyl–4–Imidazolecarboxamide I. Ring Closure with Benzoyl Isothiocyanate, J. Org. Chem. 32:1825–1828 (1967).

B. Alhede et al., "A Simple and Efficient Synthesis of 9–Substituted Guanines. Cyclodesulfurization of 1–Substituted 5–[(Thiocarbamoyl)amino] imidazole–4–carboxamides under Aqueous Basic Conditions," J. Org. Chem. 56:2139–2143 (1991).

R. Spector, "Hypoxanthine Transport and Metabolism in the Central Nervous System," J. Neurochem. 50: 969–978 (1988).

D. Triguero et al., "Capillary Depletion Method for Quantitation of Blood–Brain Barrier Transport of Circulating Peptides and Plasma Proteins," J. Neurochem. 54: 1882–1888 (1990).

W.A. Banks et al., "Measurement of Efflux Rates from Brain to Blood" in Methods in Molecular Biology, Neuropeptide Protocols (G.B. Irvine & C.H. Williams, eds., Humana Press, Totowa, NJ, 1997), pp. 353–360.

M.P. Rathbone et al., "Physiology and Pharmacology of Natural and Synthetic Nonadenine–Based Purines in the Nervous System," Drug Develop. Res. 45:356–372 (1998).

M.P. Rathbone et al., AIT–082 as a Potential Neuroprotective and Regenerative Agent in Stroke and Central Nervous System Injury, Exp. Opin. Invest. Drugs 8: 1255–1262 (1999).

W.A. Banks et al., "Effects of Wheatgerm Agglutinin and Aging on the Regional Brain Uptake of HIV–1 gp120," Life Sci. 65: 81–89 (1999).

J.S. Bintner et al., "AIT–082, a Hypoxanthine Derivative, Prevents Much of the Decrease in Cerebellar Neuron ATP Following Glutamate Exposure," Soc. Neurosci. 25: 2131 (1999) (abstract).

R. Huang et al., "Enhancement of Neuronal Cell Excitability by AIT–082 in Rat Hippocampal Neurons and Its Effects on Second Messenger System," Soc. Neurosci. 24: 1941 (1998) (abstract).

O.Chu–LaGraff et al., "Effect of AIT–082 on Brain NGF mRNA Levels and Transport of AIT–082 Across the Blood–Brain Barrier," Soc. Neurosci. 24: 1941 (1998) (abstract).

F. Caciagli et al., "The Hypoxanthine Derivative AIT–082 Protects Against Neurotoxicity in Vitro and in Vivo," Soc. Neurosci. 24: 1941 (1998) (abstract).

B.H.J. Juurlink et al., "The Hypoxanthine Analogue AIT–082 Promotes Neurite Formation and Regeneration in Cultured Hippocampal Neurons," Soc. Neurosci. 24: 1941 (1998) (abstract).

E.M. Taylor et al., "$^{14}$C–AIT082 Crosses the Blood–Brain Barrier and Is Pumped Out of Brain by a Probenecid—and Verapamil–Sensitive Mechanism," Soc. Neurosci. 25: 1758 (1999) (abstract).

F. Caciagli et al., "The Hypoxanthine Analogue AIT–082 Mimics the Activity of Guanosine in Affecting Extracellular Adenosine Breakdown and Glutamate Reuptake in Rat Cultured Astrocytes," Soc. Neurosci. 25: 1195 (1999) (abstract).

R. Ciccarelli et al., "Guanosine and Related Drugs Stimulate the Production of Neurotrophic Factors from Rat Cultured Astrocytes by Involving Mitogen–Activated Protein Kinase Pathway," Soc. Neurosci. 25: 1013 (1999) (abstract).

P.J. Middlemiss et al., "The Synthetic Purine AIT–082 Enhances Recovery After Acute Spinal Cord Crush Injury in Rats," Soc. Neurosci. 25: 1002 (1999) (abstract).

P. Di Iorio et al., "The Hypoxanthine Derivative AIT–082 Is Protective Against NMDA—or Kainic Acid–Induced Rat Hippocampal Neurotoxicity in Vivo," Soc. Neurosci. 25: 756 (1999) (abstract).

A.G. Gittis & J.R. Puzuasky, "AIT–082 Improves Memory Performance in a Non–Match–to–Sample Task in Rats," Soc. Neurosci. 25: 62 (1999) (abstract).

R.E. Callard & A.J.H. Gearing, "The Cytokine Facts Book" (Academic Press, London, 1994), pp. 99–100, 104–105, 191–200, 235–237.

P.J. Middlesmiss et al., "AIT–082, a Unique Purine Derivative, Enhances Nerve Growth Factor Mediated Neurite Outgrowth from PC12 Cells," Neurosci. Lett.199: 131–134 (1995).

K.L. Audus et al., "Brain Uptake of Drugs: the Influence of Chemical and Biological Factors," Adv. Drug Res. 23: 1–64 (1992).

W.A. Banks & A.J. Kastin, "Measurement of Transport of Cytokines Across the Blood–Brain Barrier," Meth. Neurosci. 16: 67–77 (1993).

A.L. Betz, "Identification of Hypoxanthine Transport and Xanthine Oxidase Activity in Brain Capillaries," J. Neurochem. 44: 574–579 (1985).

F.G. Blasberg et al., "Transport of α–Aminoisobutyric Acid Across Brain Capillary and Cellular Membranes," J. Cereb. Blood Flow Metab. 3: 8–32 (1983).

E.M. Cornford & W.H. Olendorf, "Independent Blood–Brain Barrier Transport Systems for Nucleic Acid Precursors," *Biochim. Biophys. Acta* 394: 211–219 (1975).

A.J. Glasky et al., "Effect of AIT–082, a Purine Analog, on Working Memory in Normal and Aged Mice," *Pharmacol. Biochem. Behav.* 47: 325–329 (1994).

A.J. Glasky et al., "Neurotrophins, Growth Factors and Mimetic Agents as Neuroprotectors in the Treatment of Alzheimer's Disease" in *Alzheimer Disease: From Molecular Biology to Therapy* (R. Becker & E. Giacobini, eds., Birkhäuser, Boston, 1996), pp. 119–124.

E.G. Gutierrez et al., "Murine Tumor Necrosis Factor Alpha Is Transported from Blood to Brain in the Mouse," *J. Neuroimmunol.* 47: 169–176 (1993).

M. Hosokawa & M. Ueno, "Aging of Blood–Brain Barrier and Neuronal Cells of Eye and Ear in SAM Mice," *Neurobiol. Aging* 20: 117–123 (1999).

M.D. Johnson & B.D. Anderson, "Localization of Purine Metabolizing Enzymes in Bovine Brain Microvessel Endothelial Cells: An Enzymatic Blood–Brain Barrier for Dideoxynucleosides?," *Pharm. Res.* 13: 1881–1886 (1996).

A.D. Mooradian, "Effect of Aging on the Blood–Brain Barrier," *Neurobiol. Aging* 9: 31–39 (1988).

W. Pan et al., "Permeability of the Blood–Brain Barrier to Neurotrophins," *Brain Res.* 788: 87–94 (1998).

W.M. Pardridge, "CNS Drug Design Based on Principles of Blood–Brain Barrier Transport," *J. Neurochem.* 70: 1781–1792 (1998).

J.F.Poduslo et al., "Macromolecular Permeability Across the Blood–Nerve and Blood–Brain Barriers," *Proc. Natl. Acad. Sci. USA* 91: 5705–5709 (1994).

J.F. Poduslo & G.L. Curran, "Permeability at the Blood–Brain Barrier and Blood–Nerve Barriers of the Neurotrophic Factors: NGF, CNTF, NT–3, BDNF," *Mol. Brain Res.* 36: 280–296 (1996).

J.J. Ramirez et al., "AIT–082 Accelerates Septodentate Sprouting After Unilateral Entorhinal Cortex Lesion in Rats," *Soc. Neurosci. Abstr.* 24: 1942 (1998).

G.N. Shah & A.D. Mooradian, "Age–Related Changes in the Blood–Brain Barrier," *Exp. Gerontol.* 32: 501–519 (1997).

I. Skoog et al., "A Population Study on Blood–Brain Barrier Function in 85–Year–Olds: Relation to Alzheimer's Disease and Vascular Dementia," *Neurology* 50: 966–971 (1998).

R. Spector, "Hypoxanthine Transport Through the Blood–Brain Barrier," *Neurochem. Res.* 12:791–796 (1987).

CRYSTAL FORMS OF 9-SUBSTITUTED HYPOXANTHINE DERIVATIVES

FIELD OF THE INVENTION

This invention is directed to novel crystal forms and improved synthetic methods for 9-substituted hypoxanthine compounds, particularly the 9-substituted hypoxanthine derivative 4-[[3-(1,6-dihydro-6-oxo-9H-purin-9-yl)-1-oxopropyl]amino]benzoic acid monopotassium salt (AIT-082), also designated N-4-carboxyphenyl-3-(6-oxohydropurin-9-yl) propanamide, monopotassium salt.

BACKGROUND OF THE INVENTION

There is a need for compounds that are bifunctional and that can interact with multiple receptors on the surface of different cell types. There is also a particular need for compounds that bypass the blood-brain barrier so that the activities of such compounds can be exerted in the central nervous system, such as for the treatment of diseases such as Alzheimer's disease, amyotrophic lateral sclerosis (Lou Gehrig's disease), and other neurodegenerative diseases.

A number of such compounds and methods for synthesizing them are disclosed in U.S. Pat. No. 5,091,432 to Glasky, incorporated herein by this reference. This includes a number of bifunctional compounds that cross the blood-brain barrier. Exemplary multifunctional compounds are formed from a first biologically active chemical moiety having immunological activity and a second biologically active chemical moiety having neurological activity. An exemplary immunologically active chemical moiety is hypoxanthine or purin-6(1H)-one. An additional benefit to the utilization of hypoxanthine is its structural relationship to inosine, the only purine known to cross the blood brain barrier. Hypoxanthine can be linked by a chemical bridging group, such as propionic acid or butyric acid, to a wide variety of neurologically active chemical moieties to produce a variety of compounds including 4-[[3-(1,6-dihydro-6-oxo- 9H-purin-9-yl)-1-oxopropyl]amino]benzoic acid, also referred to as N-4-carboxyphenyl-3-(6-oxohydropurin-9-yl) propanamide.

Although synthetic methods for these bifunctional compounds, including 4-[[3-(1,6-dihydro-6-oxo-9H-purin-9-yl)-1-oxopropyl]amino]benzoic acid or N-4-carboxyphenyl-3-(6-oxohydropurin-9-yl) propanamide hydrochloride were described in U.S. Pat. No. 5,091,432 to Glasky, there is a need for an improved synthetic method for these compounds. There is a particular need for a more efficient synthesis that provides higher yields and a more consistent synthesis that provides fewer side reactions as well as providing a pure and stable product.

During compound synthesis a variety of different crystalline forms of the same drug substance (polymorphism) may result. The existence of such polymorphisms is significant because different crystalline forms may have different solubility in water and thus different degrees of bioavailability in terms of pharmacokinetics (solubility) and pharmacodynamics of the compound. Therefore, compound polymorphism must be carefully checked as individual crystal structures could lead to differences in bioavailability. Therefore, there is a particular need for an analysis of the polymorphic forms of compound products and their interconversion processes. There is also a particular need for methods for producing the most stable form of compounds such as 4-[[3-(1,6-dihydro-6-oxo-9H-purin-9-yl)-1-oxopropyl]amino]benzoic acid monopotassium salt or N4-carboxyphenyl-3-(6-oxohydropurin-9-yl) propanamide monopotassium salt and for converting other crystalline and stable forms of the compound into the most stable form. All of the stable forms of this compound are pharmaceutically acceptable.

SUMMARY

One aspect of the present invention is a crystalline form of the monopotassium salt of N-4-carboxyphenyl-3(6-oxohydropurin-9-yl) propanamide monohydrate that has a solubility of about 5% (w/v) in water at 25° C., has an infrared spectrum peak from 1674.1 $cm^{-1}$ to about 1675.7 $cm^{-1}$ as measured by Fourier-transform infrared spectroscopy, and that has an X-ray powder pattern that is distinct from the X-ray powder pattern of any other crystalline form of N-4-carboxyphenyl-3-(6-oxohydropurin-9-yl) propanamide monopotassium salt, the crystalline form being designated Type I.

Another aspect of the present invention is a crystalline form of the monopotassium salt of N-4-carboxyphenyl-3-(6-oxohydropurin-9-yl) propanamide monohydrate that has a solubility of about 10% (w/v) in water at 25° C., has an infrared spectrum peak of about 1693.4 $cm^{-1}$ as measured by Fourier-transform infrared spectroscopy, and that has an X-ray powder pattern that is distinct from the X-ray powder pattern of any other crystalline form of the monopotassium salt of N-4-carboxyphenyl-3-(6-oxohydropurin-9-yl) propanamide, the crystalline form being designated Type II.

Yet another aspect of the present invention is a substantially anhydrous crystalline form of the monopotassium salt of N-4-carboxyphenyl-3-(6-oxohydropurin-9-yl) propanamide monohydrate that has less than about 1.0% water as measured by the Karl Fischer titration process, that has an infrared spectrum peak of about 1687.8 $cm^{-1}$ and that has an X-ray powder pattern that is distinct from the X-ray powder pattern of any other crystalline form of the monopotassium salt of N-4-carboxyphenyl-3-(6-oxohydropurin-9-yl) propanamide, the crystalline form being designated Type III.

Another aspect of the present invention is a method for synthesizing the Type I crystalline form of the monopotassium salt of N-4-carboxyphenyl-3-(6-oxohydropurin-9-yl) propanamide monohydrate comprising the steps of:

(1) reacting the free acid of N-4-carboxyphenyl-3-(6-oxohydropurin-9-yl) propanamide with potassium hydroxide in water; and (2) precipitating the product of step (1) with ethanol to yield the Type I crystalline form.

Yet another aspect of the present invention is another method for synthesizing the Type I crystalline form of the monopotassium salt of N-4-carboxyphenyl-3-(6-oxohydropurin-9-yl) propanamide monohydrate comprising the steps of:

(1) reacting N-4-carboxyphenyl-3-(6-oxohydropurin-9-yl) propanamide ethyl ester monoacetate with potassium hydroxide to produce N-4-carboxyphenyl-3-(6-oxohydropurin-9-yl) propanamide in a crystalline form distinct from Type I; and (2) reacting the product of step (1) with a mixture of ethanol and water containing a low concentration of potassium hydroxide to yield the Type I crystalline form of the monopotassium salt of N-4-carboxyphenyl-3-(6-oxohydropurin-9-yl) propanamide monohydrate.

Still another aspect of the present invention is a method for converting a distinct crystalline form of the monopotassium salt of N-4-carboxyphenyl-3-(6-oxohydropurin-9-yl) propanamide, designated Type II, to the Type I crystalline form of the monopotassium salt of N-4-carboxyphenyl-3-(6-oxohydropurin-9-yl) propanamide monohydrate comprising the step of equilibrating the crystalline form of the monopotassium salt of N-4-carboxyphenyl-3-(6-oxohydropurin-9-yl) propanamide designated Type II with water vapor at a temperature in a range from about 60° C. to about 80° C. for a time period of from about 36 hours to about 60 hours to yield the Type I crystalline form of the monopotassium salt of N-4-carboxyphenyl-3-(6-oxohydropurin-9-yl) propanamide monohydrate.

Preferably, in this method, the temperature is about 70° C. and the time period is about 48 hours.

Yet another aspect of the present invention is a method for converting a distinct crystalline form of the monopotassium salt of N-4-carboxyphenyl-3-(6-oxohydropurin-9-yl) propanamide, designated Type III, to the Type I crystalline form of the monopotassium salt of N-4-carboxyphenyl-3-(6-oxohydropurin-9-yl) propanamide monohydrate comprising the step of equilibrating the crystalline form of the monopotassium salt of N-4-carboxyphenyl-3-(6-oxohydropurin-9-yl) propanamide designated Type III with water vapor at about 25° C. to yield the Type I crystalline form of the monopotassium salt of N-4-carboxyphenyl-3-(6-oxohydropurin-9-yl) propanamide monohydrate.

BRIEF DESCRIPTION OF THE DRAWINGS

The following invention will become better understood with reference to the specification, appended claims, and accompanying drawings, where:

FIG. 7 shows X-ray diffraction powder patterns of various crystal forms of N-4-carboxyphenyl-3-(6-oxohydropurin-9-yl) propanamide monopotassium salt: (a) Type III (designated NTA-107-B/a); (b) Type I (designated NTA-107-B);

DESCRIPTION

Figure 1:
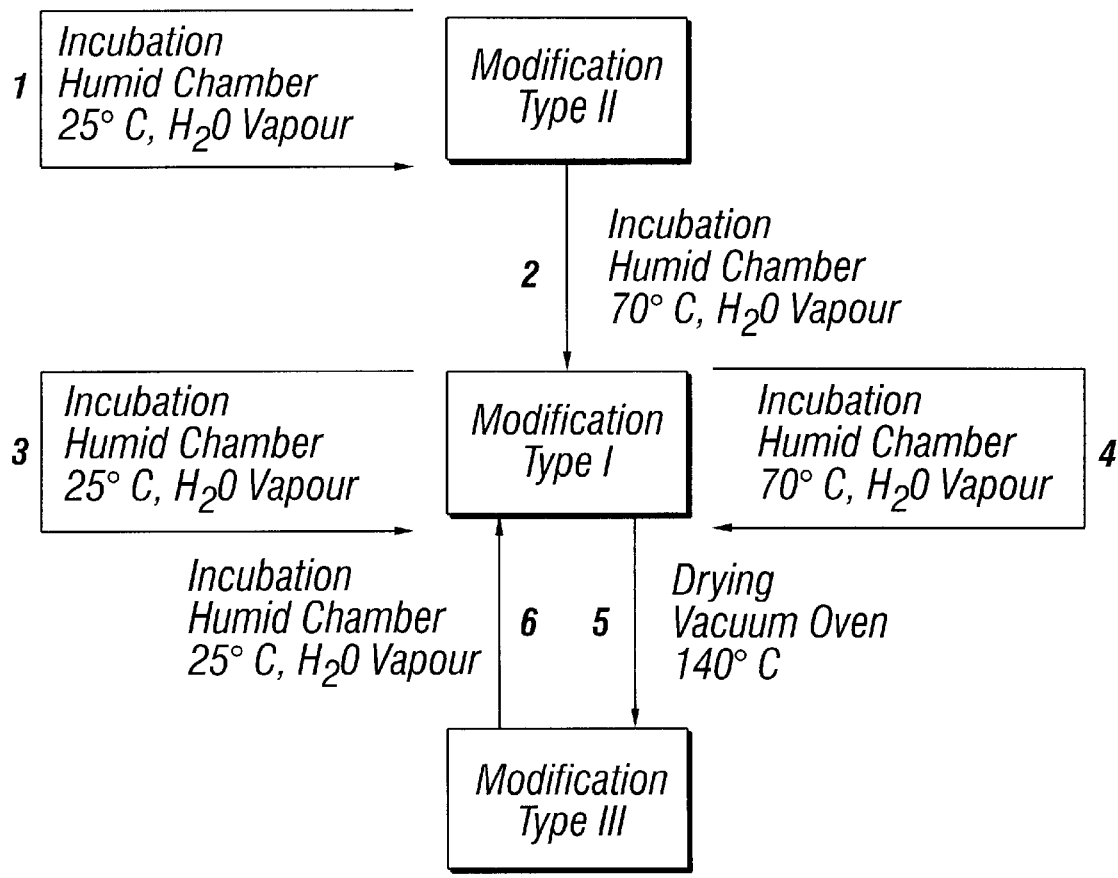
FIG. 1 is a diagram showing the interconversions between the Type I, Type II, and Type III crystal structures for N-4-carboxyphenyl-3-(6-oxohydropurin-9-yl) propanamide monopotassium salt.

The compound N-4-carboxyphenyl-3-(6-oxohydropurin-9-yl) propanamide monopotassium salt occurs in a number of different crystal forms. These forms reflect different degrees of hydration. As detailed below, there are three crystalline forms of these compound, designated as Type I, Type II, and Type III. These forms can be interconverted, also as detailed below.

Type I is a monohydrate in which the carboxyl group is in the form of a potassium salt. From the standpoint of stability, Type I is the most desirable crystal form. Therefore, it is important that manufacturing processes be developed that either result in Type I or convert other forms to Type I. Preferably, Type I is prepared under conditions that suppress deprotonation of the hydroxyl group (as a tautomer of the oxo group) of the pyrimidine ring of the molecule. If Type I is prepared at a pH value greater than about 8.5, the hydroxyl group of the pyrridine begins to deprotonate and the crystal contains a slight excess of potassium as a counterion. This leads to a variant to Type I which has a distinguishable X-ray powder pattern with an additional line.

Type II is also in the form of a monopotassium salt, but the water of hydration is not so strongly bound in the crystal lattice as that of Type I and may be considered as "adherent" water.

Type III is also in the form of a monopotassium salt, but lacks the "adherent" water and most of the water of crystallization. Type III contains about 0.850% to about 0.91% of crystal water.

The forms can be interconverted. Type II can be converted into Type I by equilibration of Type II in a humid chamber at 70° C. or by heating in a solution of water and ethanol at 70° C. Type I can be converted to Type III by strong drying conditions, such as heating under vacuum at 140° C. Type III can be converted back to Type I by humidification at 25° C. Type I is stable under treatment at either 25° C. or 70° C. in a humid chamber.

Therefore, one aspect of the present invention is a distinct crystalline form of the monopotassium salt of N-4-carboxyphenyl-3-(6-oxohydropurin-9-yl) propanamide monohydrate, This crystalline form is designated as Type I. This crystalline form has a solubility of about 5% (w/v) in water at 25° C. This crystalline form also has an infrared spectrum peak from about 1674.1 cm$^{-1}$ to about 1675.7 cm$^{-1}$ as measured by Fourier-transform infrared spectroscopy. This crystalline form also has an X-ray diffraction powder pattern that is distinct from the X-ray diffraction powder pattern of any other form of N-4-carboxyphenyl-3-(6-oxohydropurin-9-yl) propanamide monopotassium salt. This X-ray diffraction powder pattern is shown in FIG. 3(b), FIG. 3(c), FIG. 3(d), FIG. 3(f), and FIG. 3(h).

Another aspect of the present invention is a method for synthesizing the Type I crystalline form of the monopotassium salt of N-4-carboxyphenyl-3-(6-oxohydropurin-9yl) propanamide monohydrate. In general, this method comprises:

(1) reacting the free acid of N-4-carboxyphenyl-3-(6-oxohydropurin-9-yl) propanamide with potassium hydroxide in water; and (2) precipitating the product of step (1) with ethanol to yield the Type I crystalline form of the monopotassium salt of N-4-carboxyphenyl-3-(6-oxohydropurin-9-yl) propanamide monohydrate.

Preferably, this reaction takes place at about 0° C. to about 80° C.

Still another aspect of the present invention is another method for synthesizing the Type I crystalline form of the monopotassium salt of N-4-carboxyphenyl-3-(6-oxohydropurin-9-yl) propanamide monohydrate. In general, this method comprises:

(1) reacting N-4-carboxyphenyl-3-(6-oxohydropurin-9-yl) propanamide ethyl ester monoacetate with potassium hydroxide in water and then with hydrogen chloride to produce the monopotassium salt of N-4-carboxyphenyl-3-(6-oxohydropurin-9-yl) propanamide in a crystalline form that is distinct from Type I; and (2) reacting the product of step (1) with an ethanol-water mixture containing a small proportion of potassium hydroxide to produce the Type I crystalline form of the monopotassium salt of N-4-carboxyphenyl-3-(6-oxohydropurin-9-yl) propanamide monohydrate.

Preferably, the concentration of potassium hydroxide in the ethanol-water mixture is about 0.1%.

In this procedure, the crystalline form of the monopotassium salt of N-4-carboxyphenyl-3-(6-oxohydropurin-9-yl) propanamide is initially in a form that is distinct from Type I. This form is designated Type II. In Type II, the molecule is not in the form of a monohydrate and does not contain water of crystallization, as detailed above. It is possible to interconvert Type I and Type II, as described above and in the Example.

Still another aspect of the present invention is a method of converting the Type II crystalline form of the monopotassium salt of N-4-carboxyphenyl-3-(6-oxohydropurin-9-yl) propanamide into the Type I crystalline form of the monopotassium salt of N-4-carboxyphenyl-3-(6-oxohydropurin-9-yl) propanamide monohydrate. This method comprises heating II crystalline form in the presence of water vapor at a temperature of from about 60° C. to about 80° C. for a period of from about 36 hours to about 60 hours. Preferably, the temperature is about 70° C. and the period of the interconversion is about 48 hours. This conversion results in the insertion of water of hydration into the crystal lattice.

Another aspect of the present invention is the Type II crystalline form. The Type II crystalline form has a solubility of about 10% (w/v) in water at 25° C., has an infrared spectrum peak of about 1693.4 cm$^{-1}$ as measured by Fourier-transform infrared spectroscopy, and that has an X-ray powder pattern that is distinct from the X-ray powder pattern of any other crystalline form of the monopotassium salt of N-4-carboxyphenyl-3-(6-oxohydropurin-9-yl) propanamide.

Figure 3A:
FIG. 3 shows X-ray diffraction powder patterns of various crystal forms of N-4-carboxyphenyl-3-(6-oxohydropurin9yl) propanamide monopotassium salt: (a) Type II (designated Am 927/a) and Type I (designated DD-477-21-5); (b) Type I (designated DD-477-21-5); (c) Type II (designated Am 927/a RT) after incubation of Type II of (a) at 25° C.; Type I (designated DD-477-21-5) after incubation of Type I of (a) at 25° C.; (d) Type I (designated Am 927/a 70° C.) after incubation of Type II of (a) at 70° C.; Type I (designated DD-477-21-5 70° C. after incubation of Type I at 70° C.; (e) Type I containing admixture of dipotassium salt (designated Am 964/b); (f) Type I (designated NTA-107/B); (g) Type II (designated NTA-107/A); (h) Type I as in (f) (designated NTA 107-B); Type III (designated NTA-107-B/2) produced by heating of Type I under vacuum at 140° C.
Figure 3A:
Figure 3B:
Figure 3C:
Figure 3C:
Figure 3D:
Figure 3D:
Figure 3E:
Figure 3F:
Figures 3G, 3H, 7:
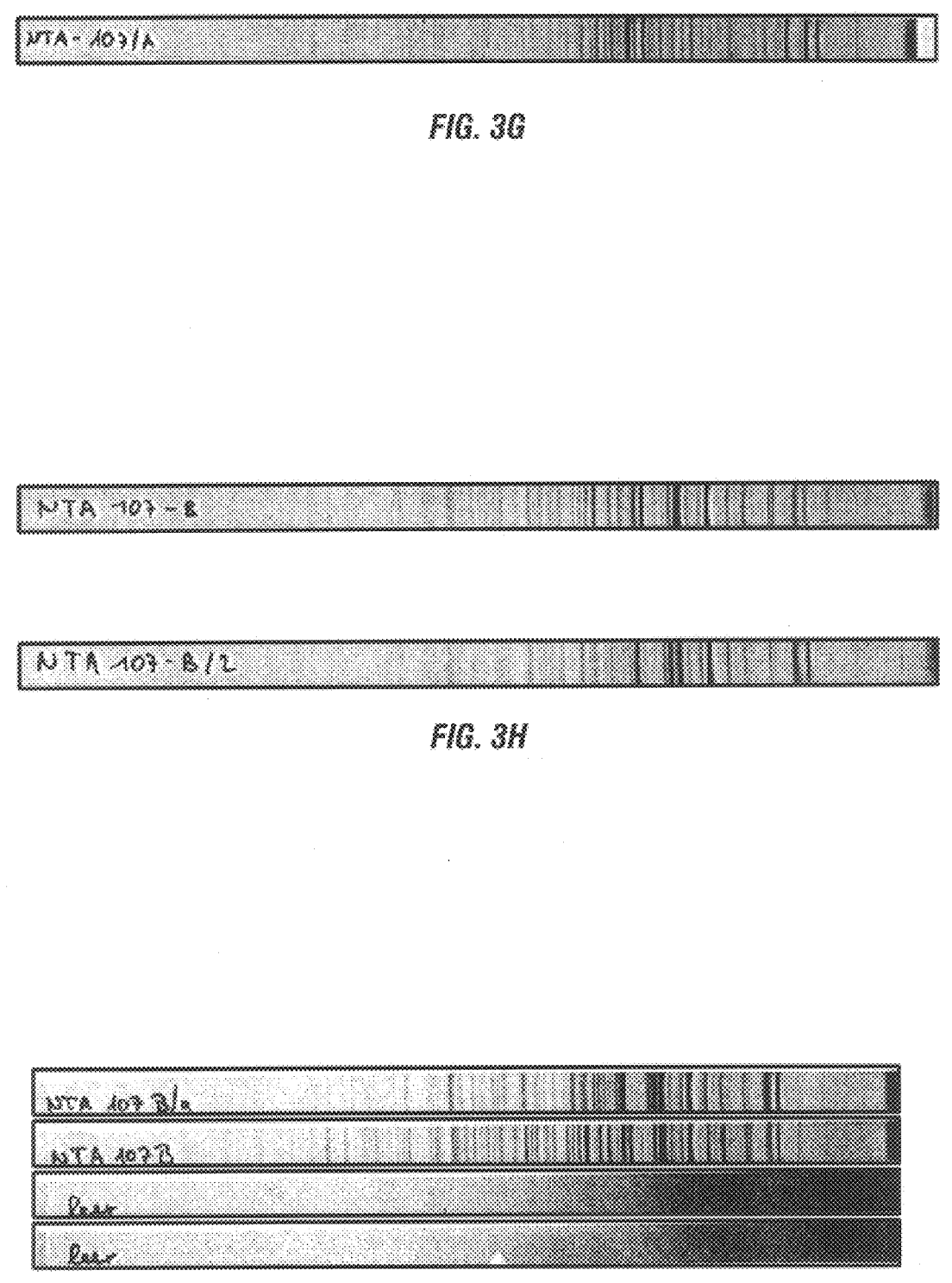
Figure 4A:
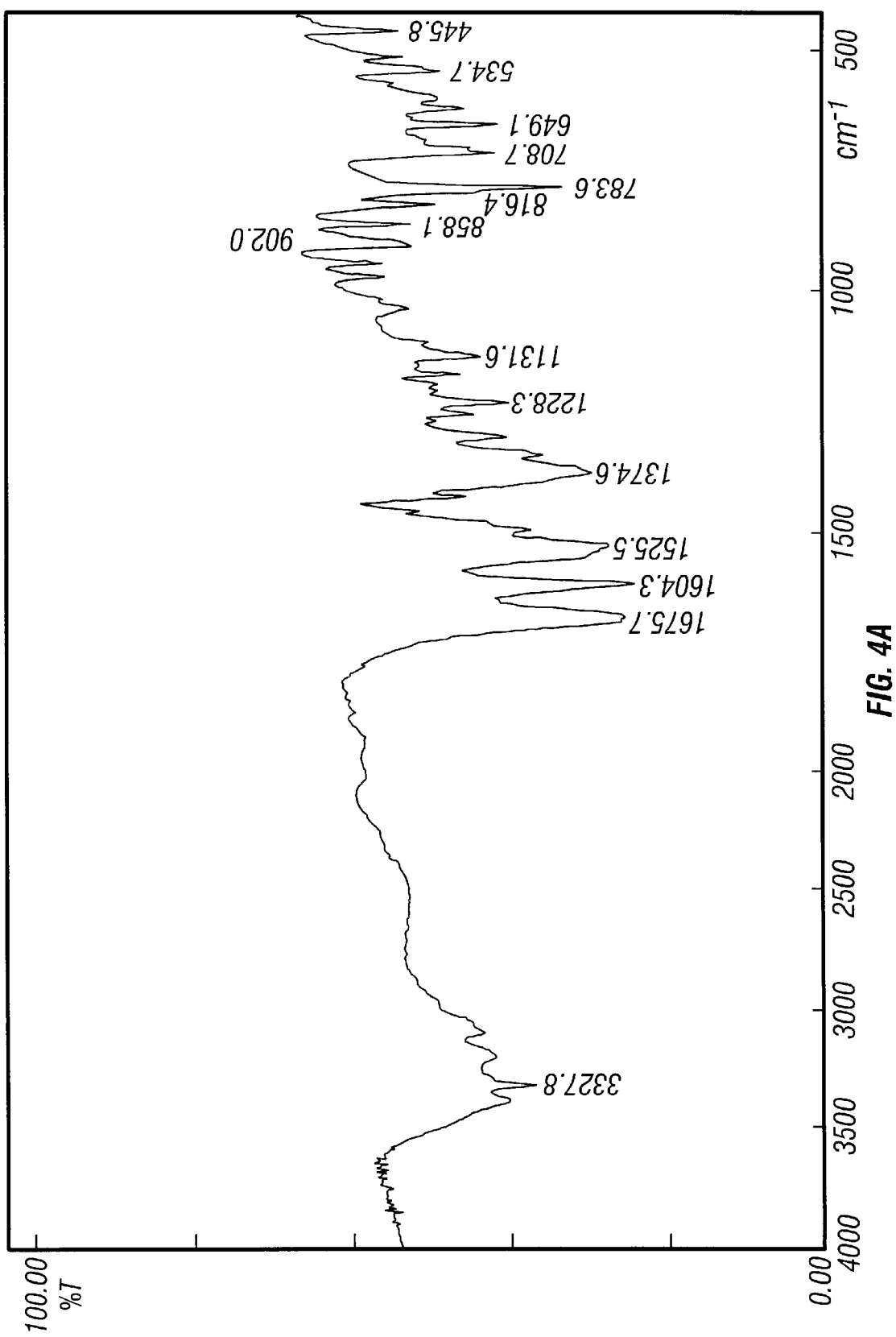
FIG. 4 shows Fourier-transform infrared spectra of various crystal forms of N-4-carboxyphenyl-3-(6-oxohydropurin-9-yl) propanamide; (a) Type I (designated DD-477-21-5); (b) Type I, second preparation (designated NTA-107-B); (c) Type I with admixture of dipotassium salt (designated Am 964/b); (d) Type II (designated Am 972/a); (e) Type II, second preparation (designated NTA-107-A)
Figure 4B:
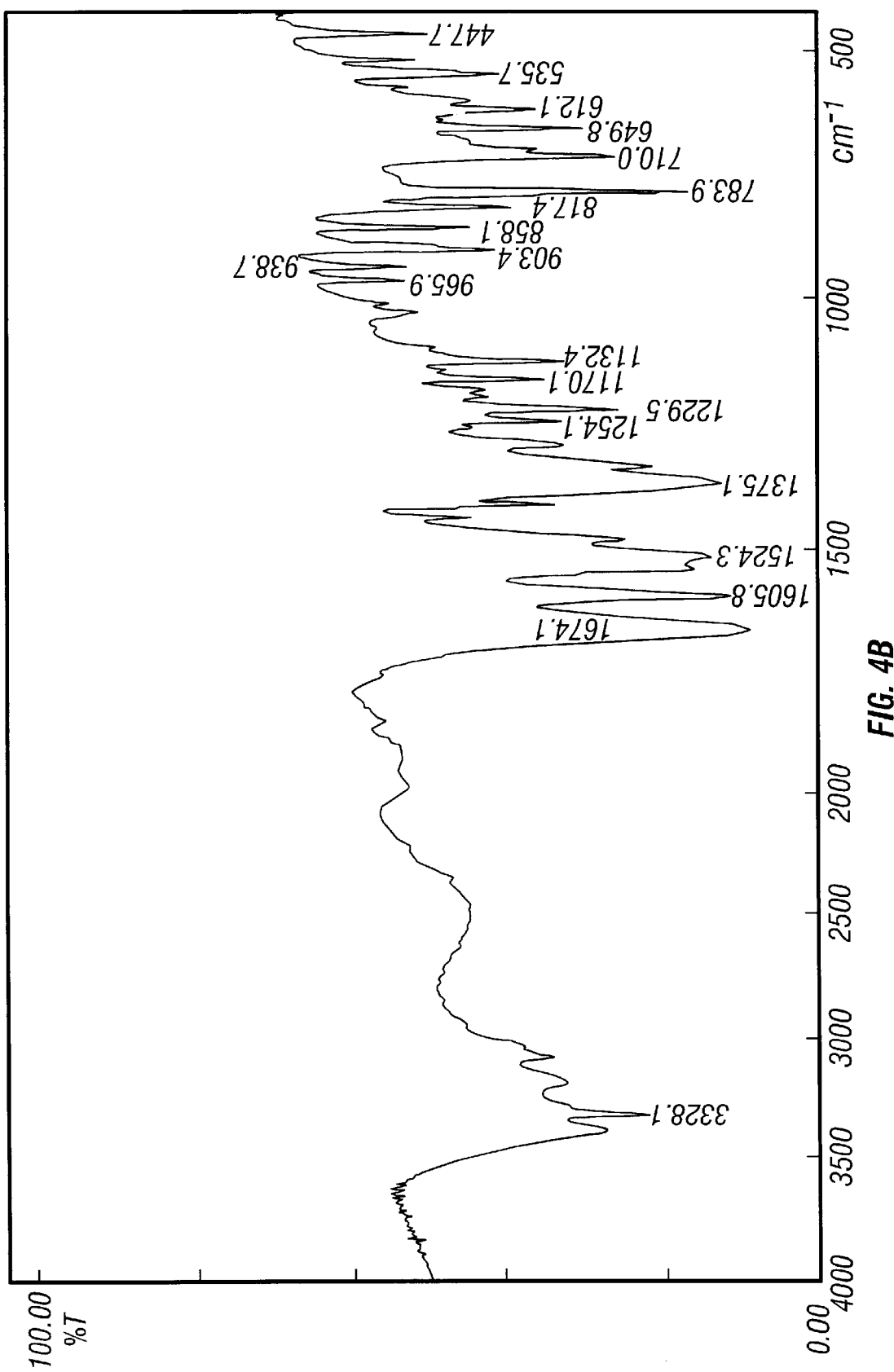
Figure 4C:
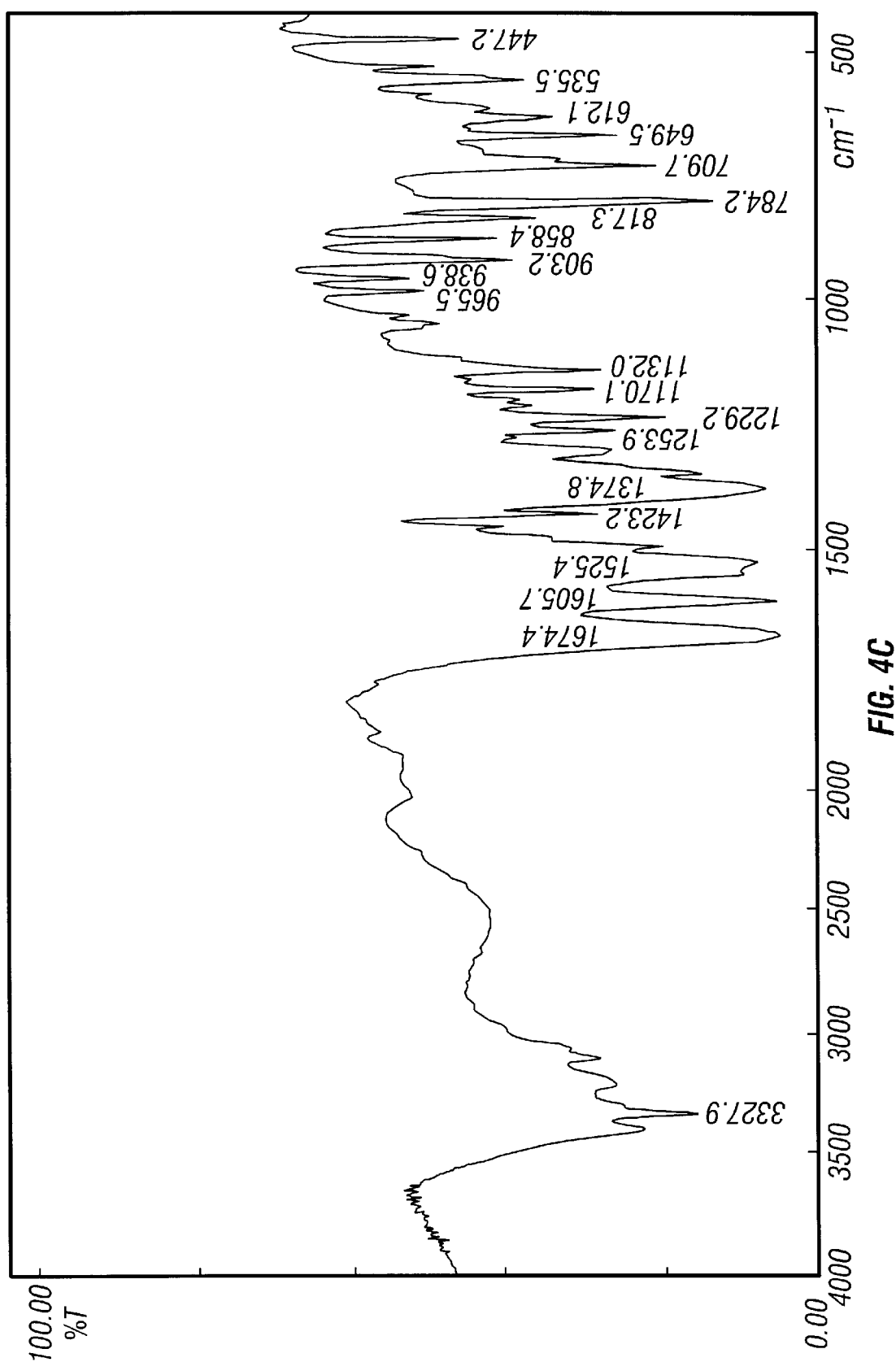
Figure 4D:
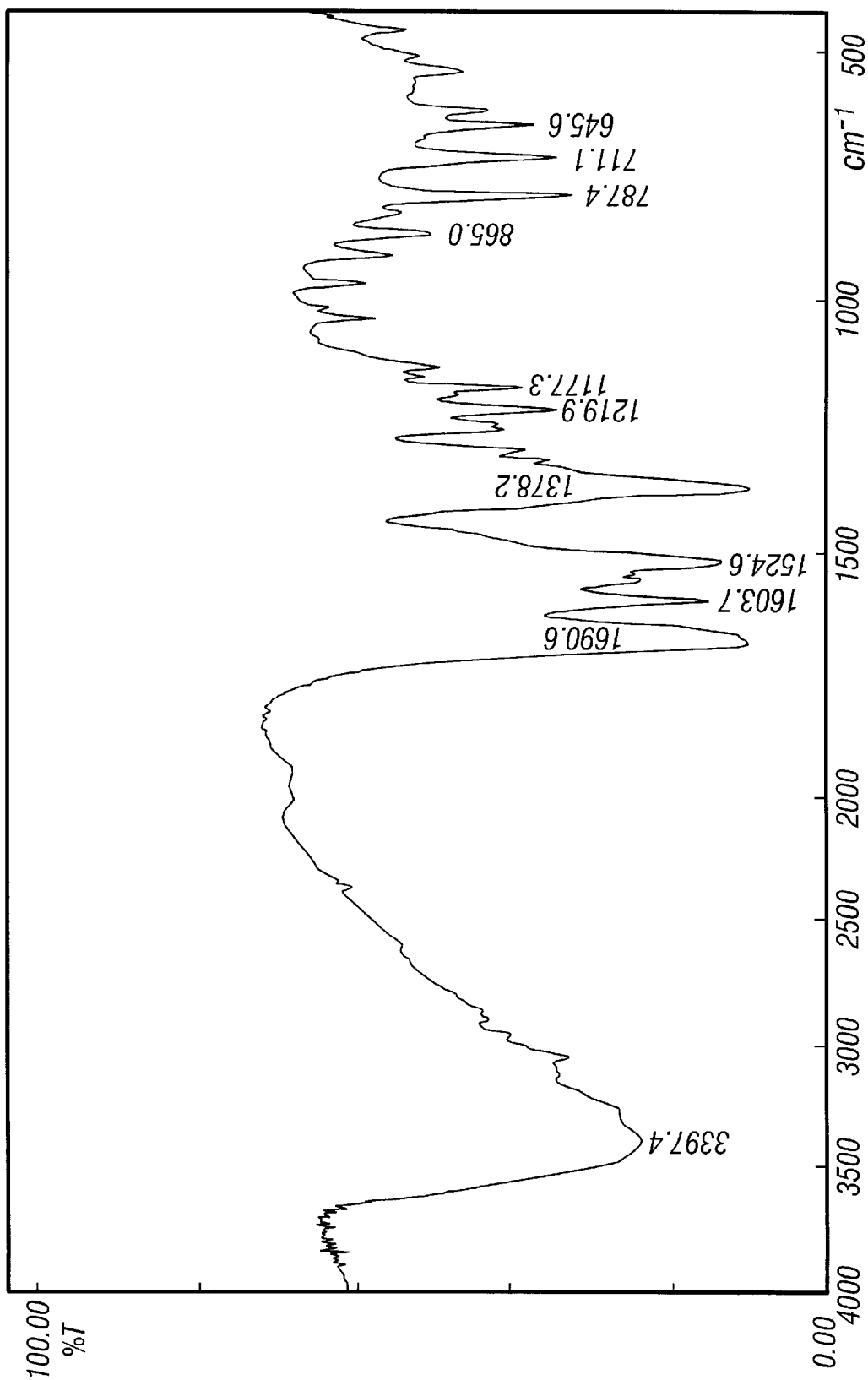
Figure 4E:
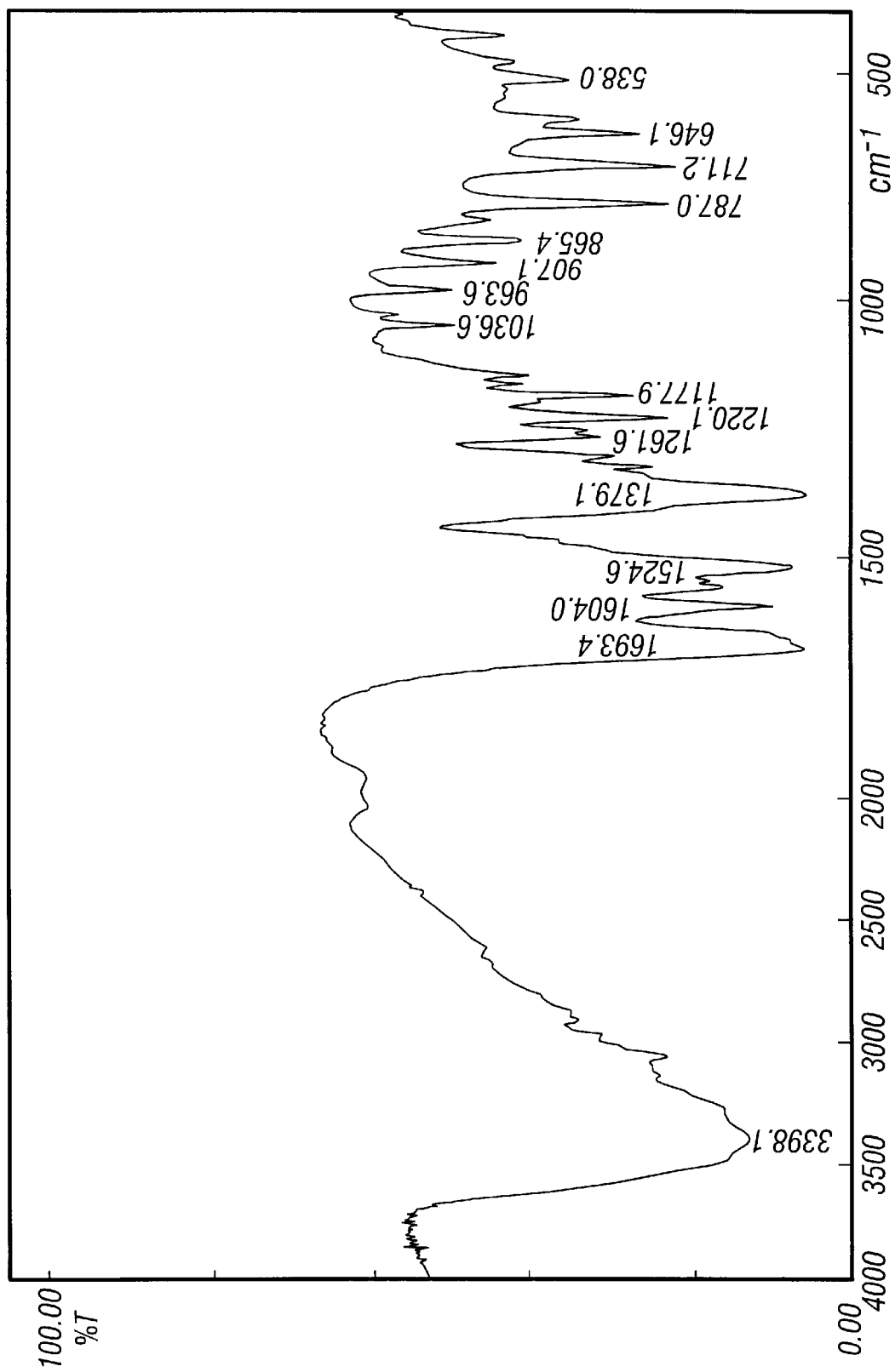

The X-ray diffraction powder pattern for Type II is shown in FIGS. 3(a), 3(c), and 3(g).

There is yet another crystal form of the monopotassium salt of N-4-carboxyphenyl-3-(6-oxohydropurin-9-yl) propanamide, designated Type III. Type III is substantially anhydrous, having a water content of less than about 1.0% as measured by Karl Fischer titration or by thermogravimetric analysis. Type III has an X-ray diffraction powder pattern distinct from that of Type I or Type II. Type III has an infrared spectrum peak of about 1687.8 cm$^{-1}$ as measured by Fourier-transform infrared spectroscopy. Type III can be converted into Type I by incubation in the presence of water vapor at a temperature of about 25° C., while Type I can be converted into Type III only by drying in a vacuum oven at a temperature of about 140° C. Type III can be readily converted back to Type I by incubation in a humid chamber at 25° C.

The X-ray diffraction powder pattern of Type III is shown in FIG. 3(h) and in FIG. 7(a).

Therefore still another aspect of the present invention is a method of converting the Type III crystalline form of the monopotassium salt of N-4-carboxyphenyl-1-(6-oxohydropurin-9-yl) propanamide into the Type I crystalline form of the monopotassium salt of N-4-carboxyphenyl-3-(6-oxohydropurin-9-yl) propanamide monohydrate by incubating the Type I crystals at a temperature of about 25° C. in the presence of water vapor.

The pattern of interconversions of Type I, Type II, and Type III crystal structures is shown in FIG. 1.

The invention is illustrated by the following Example. This Example is presented for exemplification only and are not intended to limit the invention.

EXAMPLE

Polymorphic Forms of Crystals of N-4-Carboxyphenyl-3-(6-Oxohydropurin-9-yl) Propanamide Monopotassium Salt Materials and Methods The occurrence of polymorphic forms can be examined by various physico-chemical investigation techniques. The solubility measured under defined conditions can provide information regarding the occurrence of different crystal structures. However, the preferred technique for the investigation of the polymorphism of N-4-carboxyphenyl-3-(6-oxohydropurin-9-yl) propanamide monopotassium salt is the analysis of the X-ray diffraction powder diagrams, which allows the distinct crystal structures to be clearly distinguished by their characteristic powder patterns. The powder pattern, position, intensity and sharpness of the bands are dependent upon the crystal structure and the fine arrangement of the atoms in the crystal lattice, which in turn are both influenced by the content of crystal water. For this study, material from different batches of N-4-carboxyphenyl-3-(6-oxohydropurin-9-yl) propanamide monopotassium salt was used, either in the original or in a dry or wet state (Table 1).

The water content was determined by Karl Fischer (KF) titration (Titroprocessor Metrohn 682 and Karl-Fischer Titrator Metrohm 701 Titrino) or thermogravimetric (TG) analysis (Mettler TG 50 Thermobalance).

X-ray powder patterns were measured with a β-Generator Philips PW 1120/90 equipped with a CuK$_\alpha$ Guinier-de Wolff Camera No. 11 (Enraf-Nonius).

Characterization of the thermal stability (loss of water, melting point) of different polymorphic forms was performed by differential scanning calorimetric (DSC) measurements (Mettler DSC 821) and infrared spectra (IR) were recorded on a Fourier-transform (FT) infrared spectrophotometer (erkin Elmer FT-IR Spectrometer Paragon 1000).

Synthesis

A. Via Free Acid

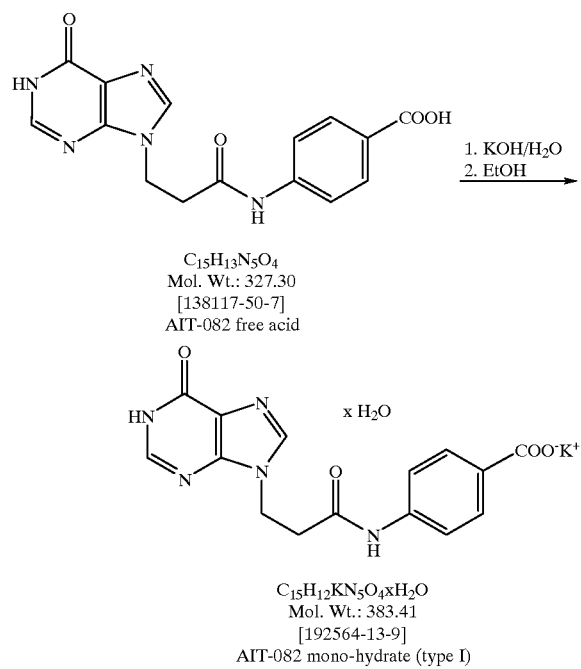

Studies with the N-4-carboxyphenyl-3-(6-oxohydropurin-9-yl) propanamide monopotassium salt revealed that the Type I crystal structure is obtained by the synthetic route depicted above. Type I form is identical to the crystal structure of the reference compound lot DD-477-21-5

B. Via Ethyl Ester Monoacetate

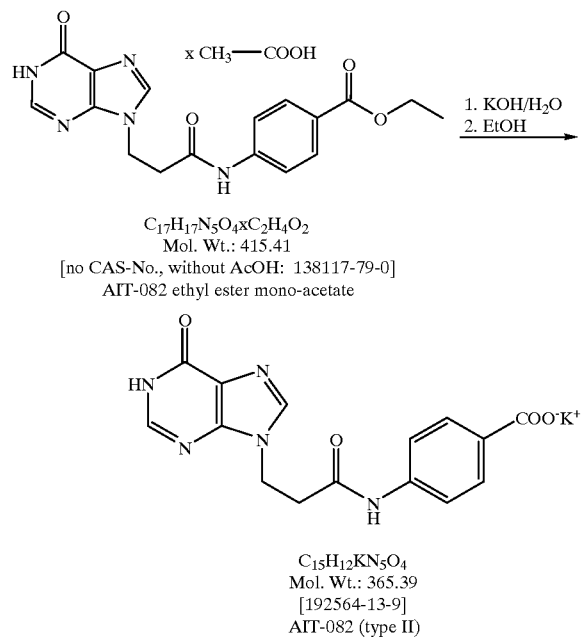

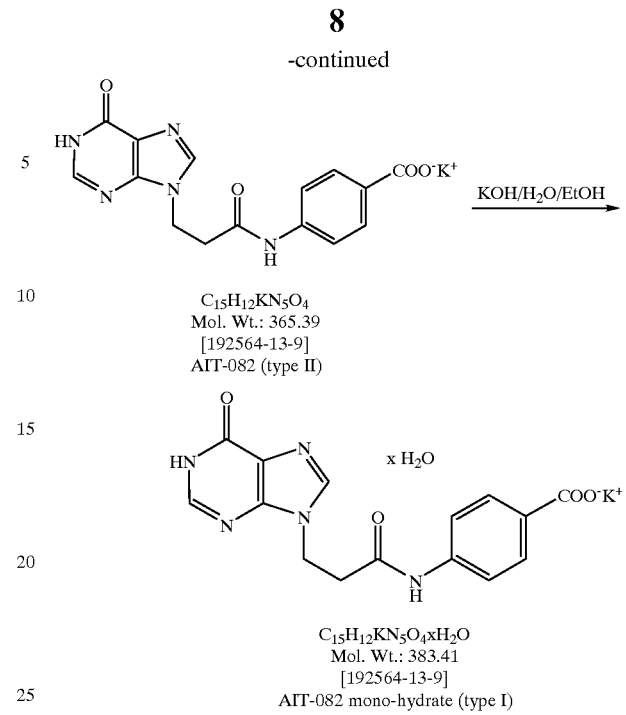

The hydrolysis of the N4-carboxyphenyl-3-(6oxohydropurin-9-yl) propanamide ethyl ester and the subsequent isolation of the N-4-carboxyphenyl-3-(6-oxohydropurin-9-yl) propanamide monopotassium salt affords the Type II crystal stricture which must be converted to the Type I modification at elevated temperature (70° C.) in a solvent mixture of ethanol/water in order to get the N-4-carboxyphenyl-3-(6-oxohydropurin-9-yl) propanamide monopotassium salt monohydrate (Type I). Without addition of water no interconversion of the crystal structure of Type II to Type I was observed. The synthetic route depicted above is preferably used in the manufacturing process and preferably includes a small amount of KOH in the final interconversion step in order to meet the solubility requirements of the active pharmaceutical ingredient.

Results

Polymorphism

Starting from different crystal structures, hydration and dehydration studies were performed (FIG. 1, Table 2). The crystal structure designated Type I (lot NTA-107-B) is obtained by equilibration of Type II (lot NTA-107-A) with water vapor in a humid chamber, whereas Type III was generated by dehydration of Type I in a vacuum drying oven at elevated temperature (Tables 1 and 2). The X-ray powder patterns of the Type I and II crystal structures are not sensitive to small changes in the water content and appear uniform from batch to batch. Starting from Type I, humidification leads to unchanged Type I, whereas under strong drying conditions (temperature and vacuum) Type III was obtained. The latter process is fully reversible and Type III turns completely into Type I upon humidification at 25° C.

Incubation of the Type I and II crystal structures in a humid chamber ($H_2O$ vapor) at 25° C. and 70° C. for 48 h resulted in the interconversion of Type II into Type I crystal structure only at elevated temperature, whereas Type I remains unchanged. Heating of AIT-082 Type II in a solution containing water and ethanol to 70° C. leads to the interconversion of Type II into Type I crystal structure. The well-resolved powder diagrams of these two forms indicate well ordered crystal lattice structures (FIG. 3). The Type I crystal structure contains about 5.8% (w/w) water and is only slightly hygroscopic. The manufacturing process leads to a water-soluble (5% w/v) crystalline product of the monopotassium salt of N-4-carboxyphenyl-3-(6-oxohydropurin-9-yl) propanamide monohydrate Type I (active pharmaceutical ingredient). N-4-carboxyphenyl-3-(6-oxohydropurin-9-yl) propanamide monopotassium salt exists, as known so far, in three different crystal structures (Types I–III) depending upon the water content. The corresponding powder diagrams exhibit well-resolved patterns with a strong peak intensity against a relatively low background. These powder patterns are shown in FIG. 3.

If the K-salt formation is performed at a pH value higher than 8.5, the oxo-group (hydroxyl-group) of the pyrimidine ring is also prone to salting. Samples which have been prepared under these reaction conditions contain a slight excess of K (di-K-salt of N-4-carboxyphenyl-3-(6-oxohydropurin-9-yl) propanamide free acid) and show an extra band in the powder diagrams (Table 1 and FIG. 3(e)).

Figure 5A:
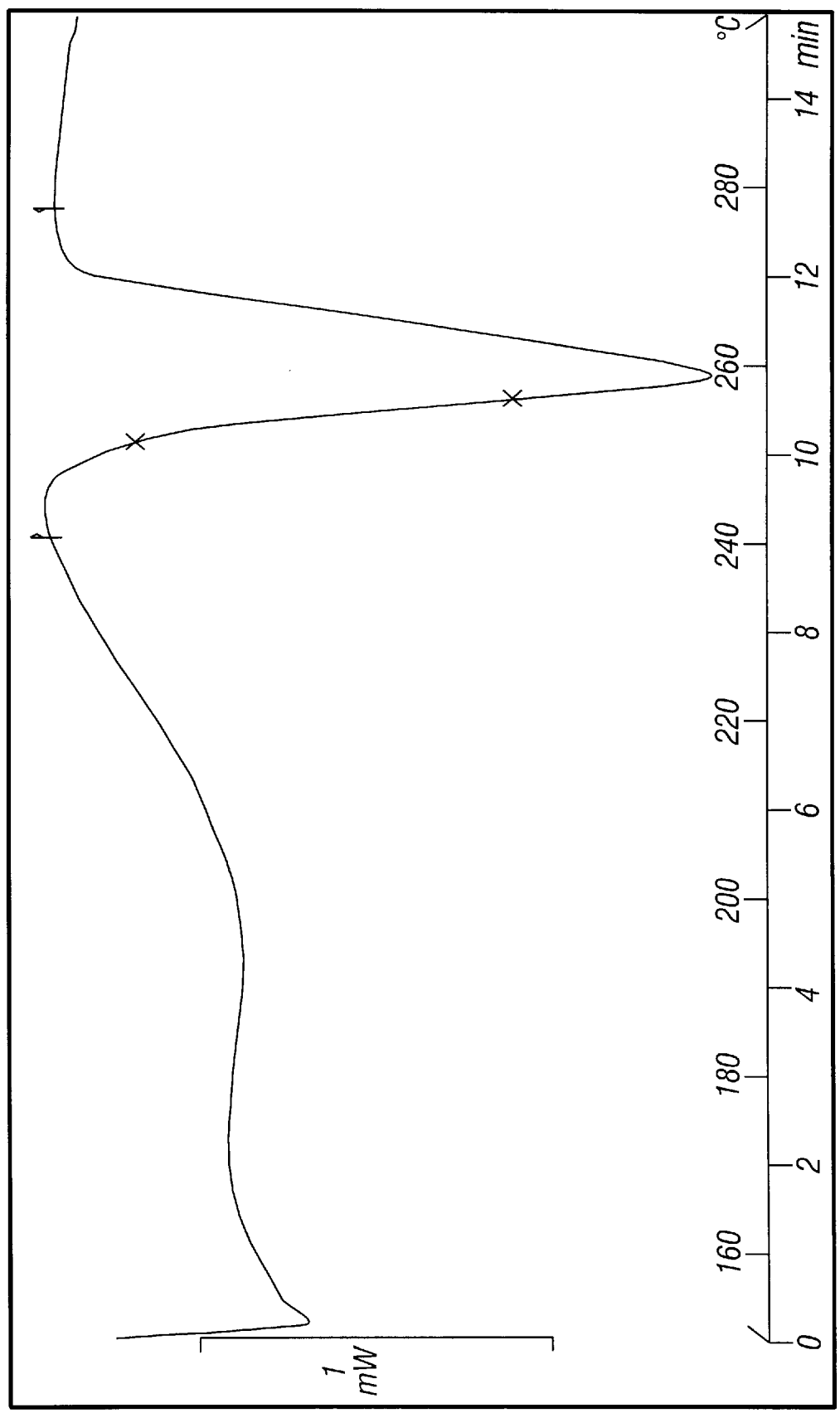
FIG. 5 shows differential scanning calorimetric (DSC) measurements on various crystal forms of N-4-carboxyphenyl-3-(6-oxohydropurin-9-yl) propanamide: (a) Type I (designated NTA-107-B), (b) Type I, second preparation (designated DD-477-21-5); (c) Type II (designated NTA- 107-A)
Figure 5B:
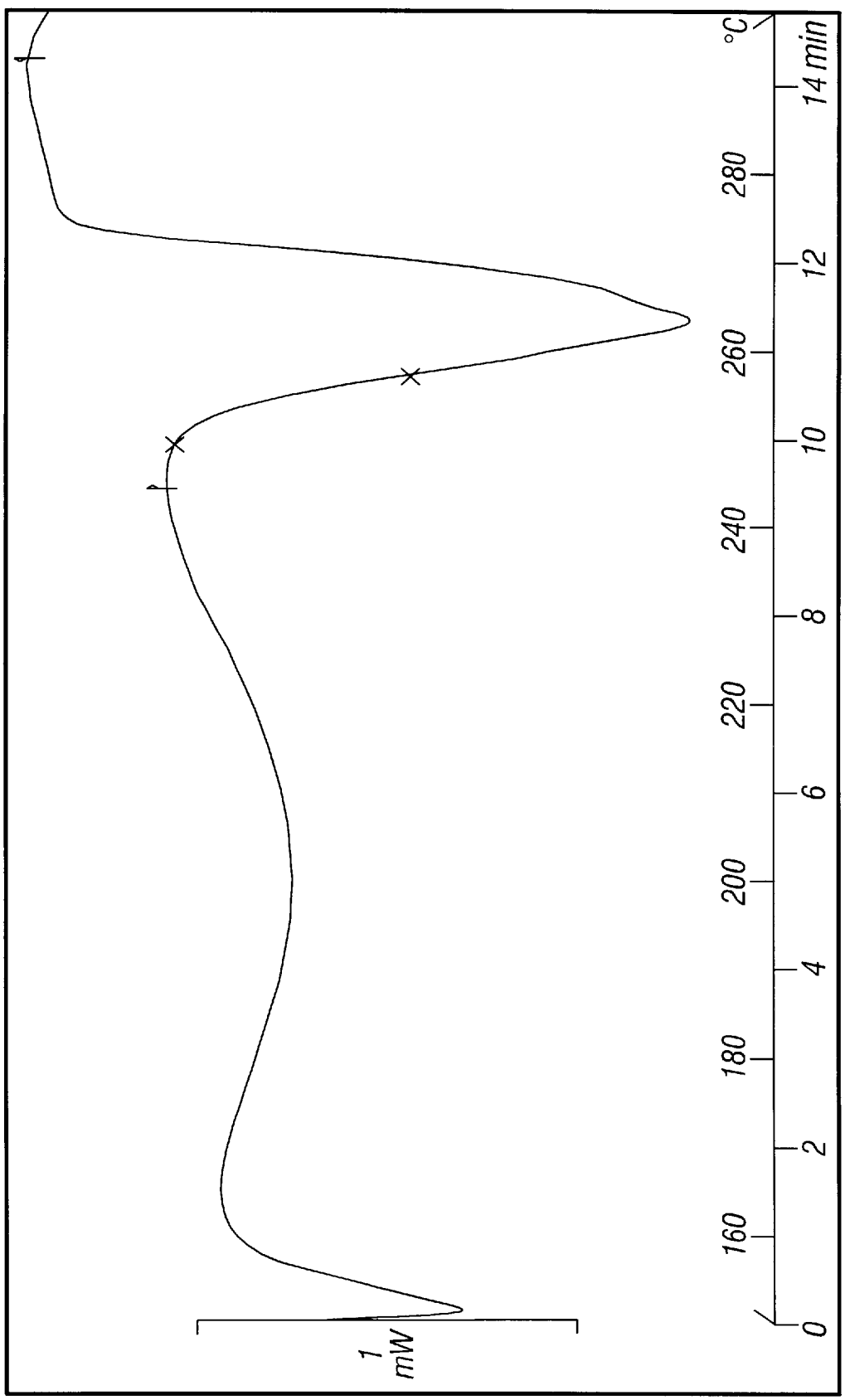
Figure 5C:
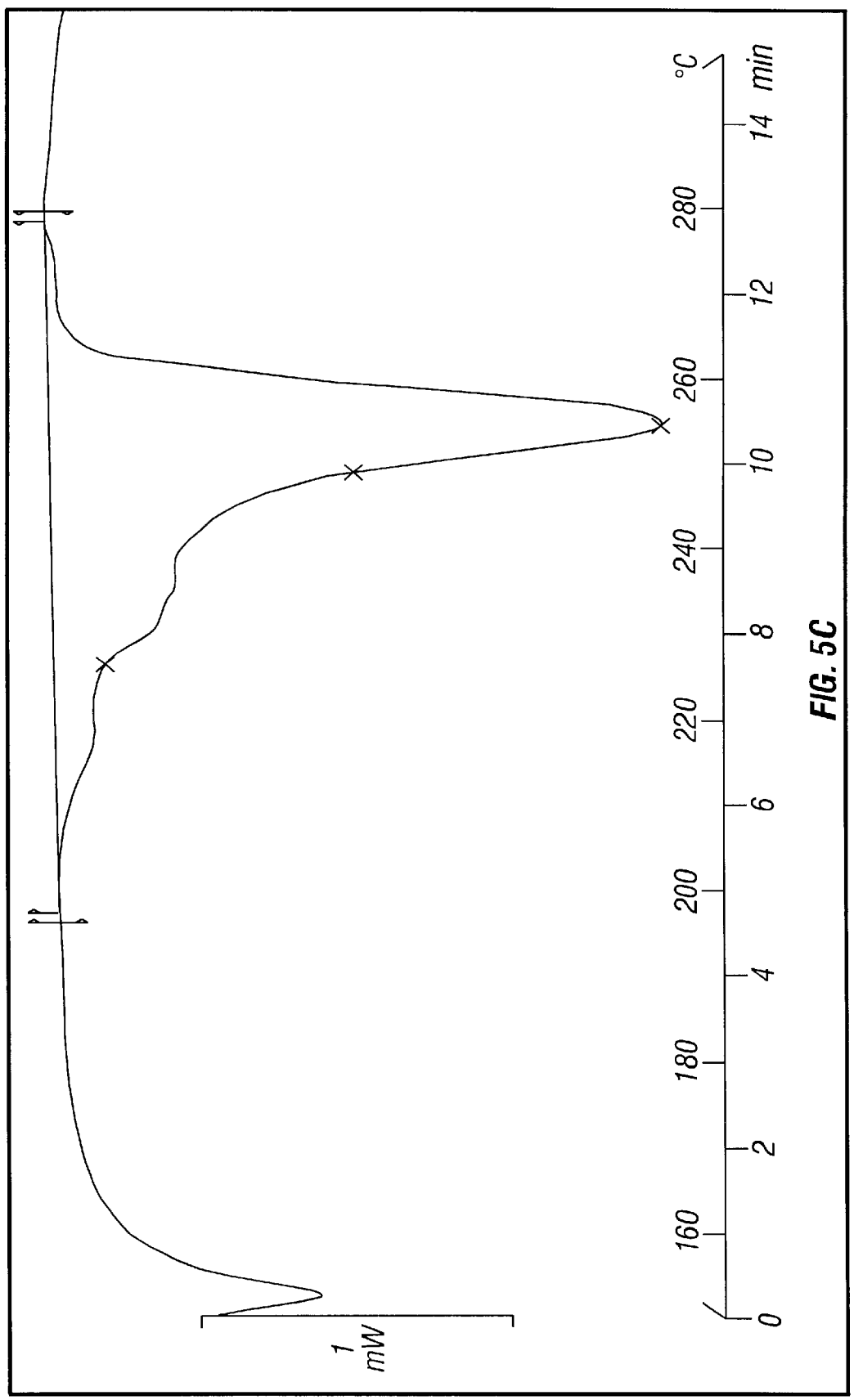
Figure 6A:
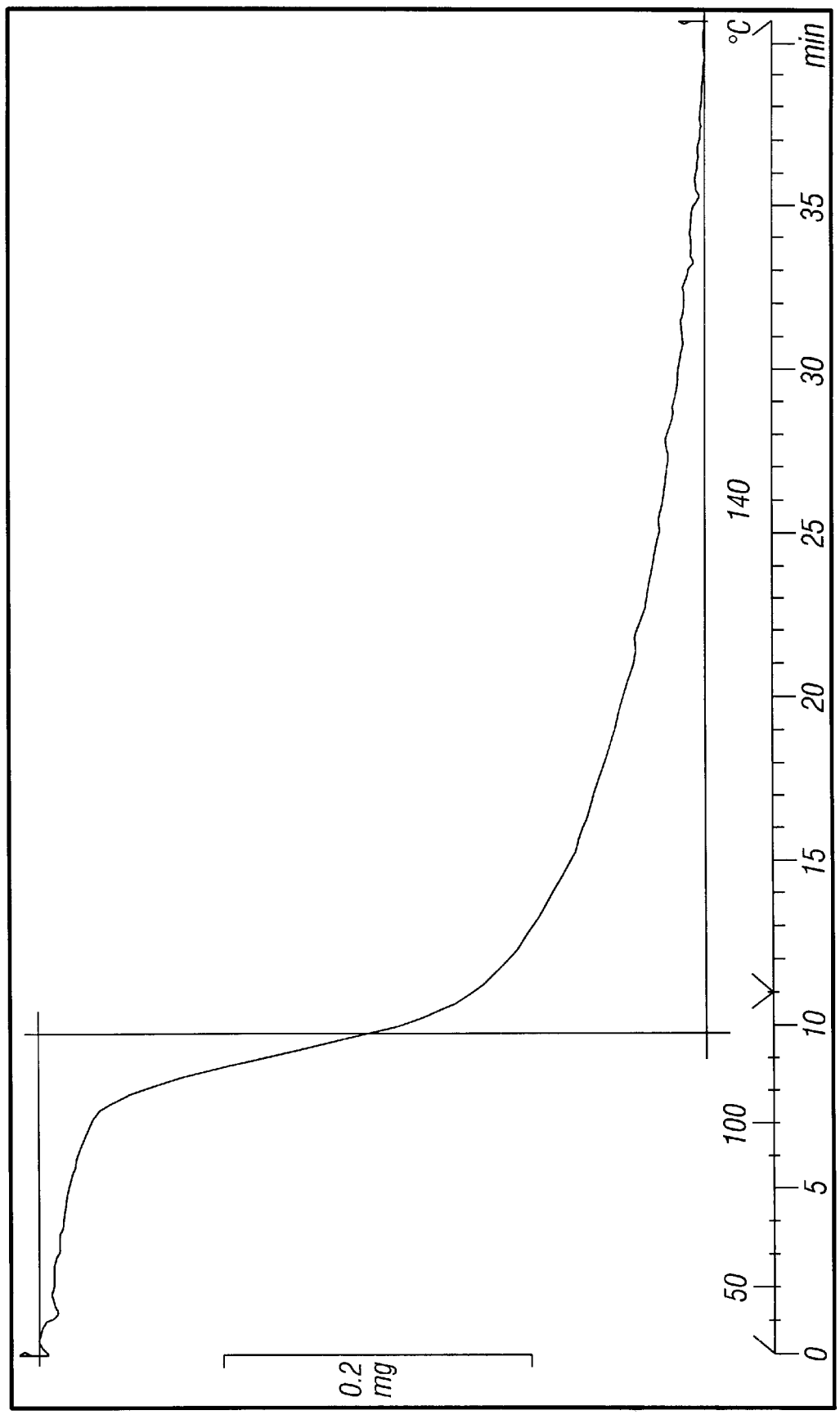
FIG. 6 shows thermogravimetric (TG) plots of mass against temperature for various crystal forms of N-4-carboxyphenyl-3-(6-oxohydropurin-9-yl) propanamide: (a) Type I (designated NTA-107-B); (b) Type I, second preparation (designated DD-477-21-5); (c) Type II (designated NTA107-A), (d) Type I with admixture of dipotassium salt (designated AM 964/b)
Figure 6B:
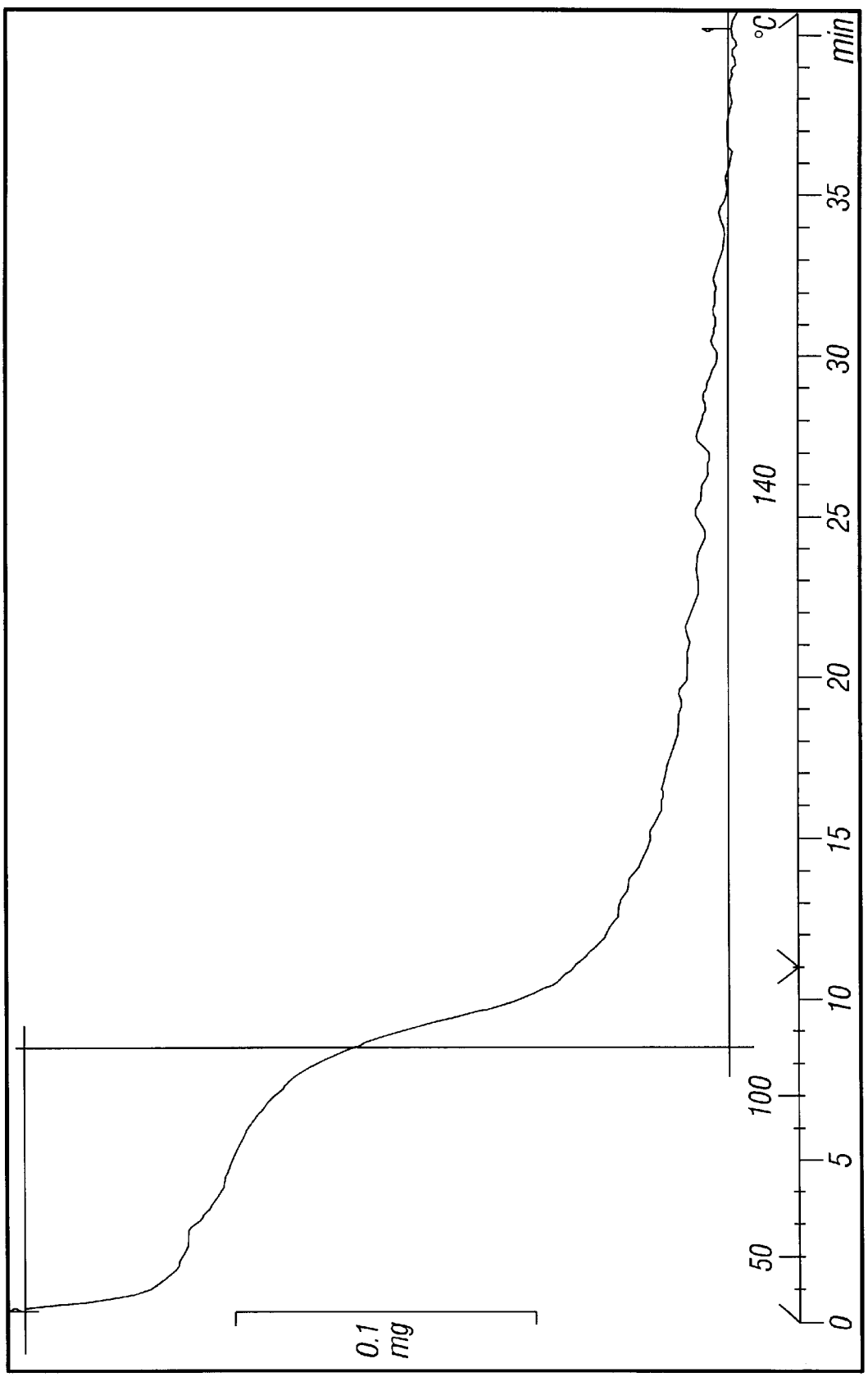
Figure 6C:
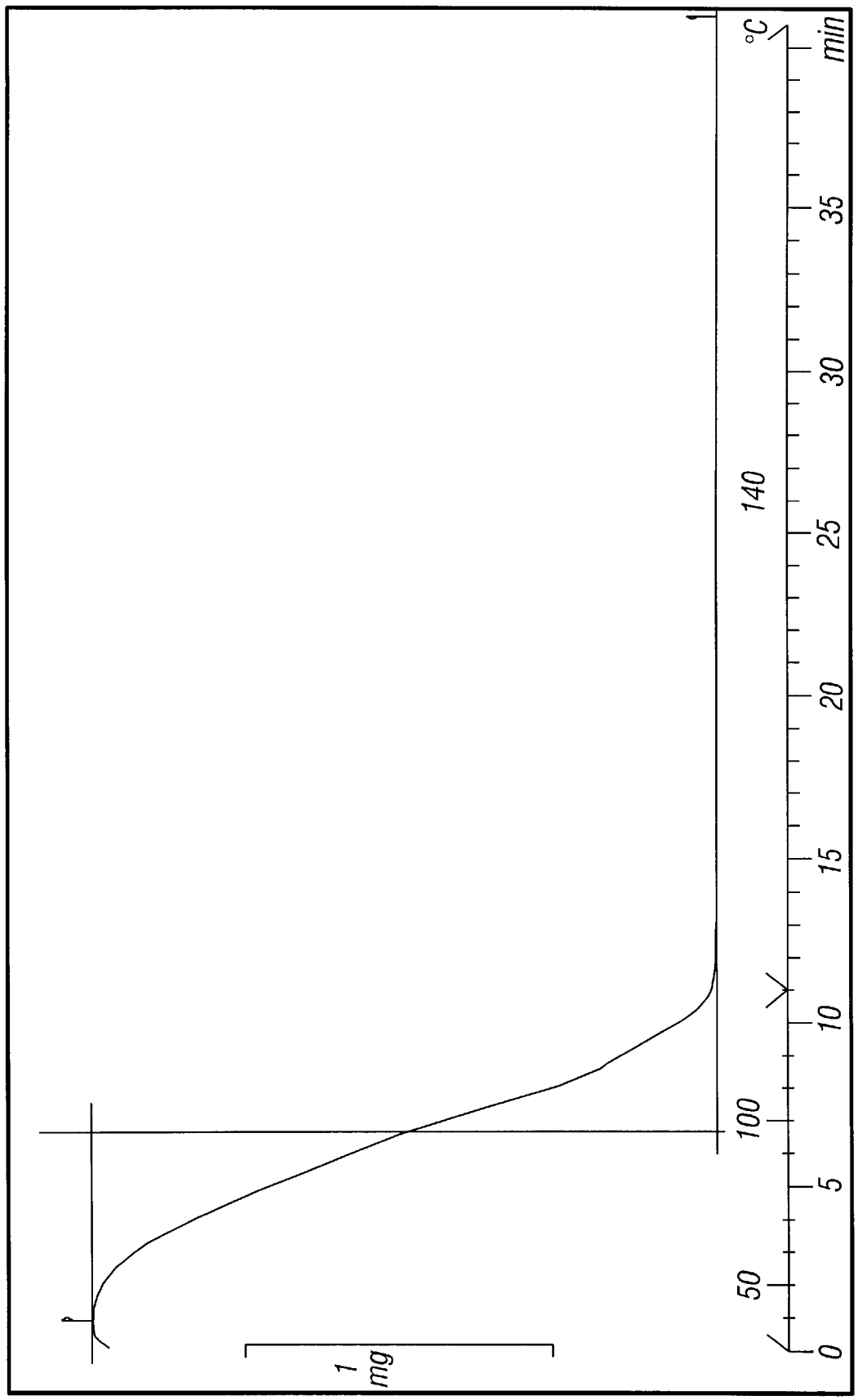
Figure 6D:
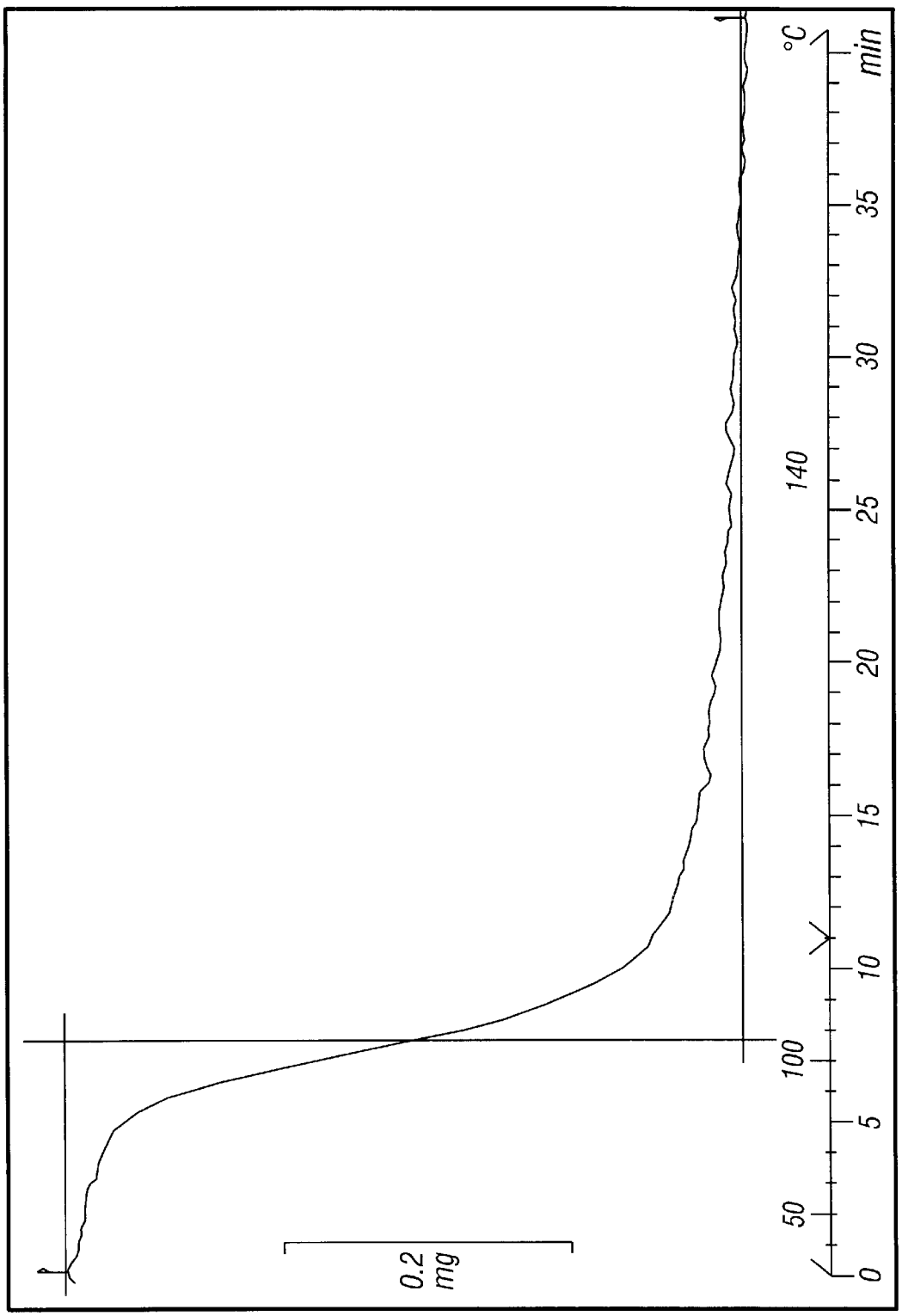

In addition to X-ray powder diffraction, IR-spectroscopy can also be used to distinguish the Type I and II crystal structure polymorphisms (FIG. 4). Type I (same as the reference compounds lot DD-477-21-5 and lot 1024.D.96.2) exhibits a characteristic IR-band centered at from about 1674.1 $cm^{-1}$ to about 1675.7 $cm^{-1}$, whereas the corresponding band of the Type II crystal structure is shifted to 1692 $cm^{-1}$. Incubation of the Type II crystal structure in a humid chamber ($H_2O$) at 25° C. and 70° C. for 48 h resulted in an interconversion of Type II into Type I only at elevated temperatures. These findings might be explained by the incorporation of water into the crystal lattice, a process which requires a relatively high energy input. It is interesting to note, that the determination of the water content of Type I and II by two different analytical methods (KF and TG) reveals a different water content only for Type I (Table 1). Tightly bound (structural) crystal water in the Type I crystal lattice might be a possible explanation for this phenomenon. DSC spectra of Type I and II are different showing a slow evaporation of the tightly-bound crystal water in Type I (FIG. 5). In contrast, the Type II structure probably contains only "adherent" water which can be evaporated under normal TG conditions (FIG. 6). The residual organic solvent (ethanol) content of both samples is rather low in both structures.

The water content of crystalline N-4-carboxyphenyl-3-(6-oxohydropurin-9-yl) propanamide monopotassium salt lies in a relatively broad range between 5–12% (w/w) depending on the type of crystal structure. A difference corresponding to one equivalent of crystal water was found in the Type I form of the monopotassium salt of N-4-carboxyphenyl-3-(6-oxohydropurin-9-yl) propanamide monohydrate upon determination of the water content by KF and TG. This result shows that a 1:1 stoichiometric mixture of structurally bound water and N-4-carboxyphenyl-3-(6-oxohydropurin-9-yl) propanamide monopotassium salt requires relatively strong drying conditions to remove the water (temperature and vacuum) because the water molecules are in a structurally tightly-bound form. It is not known whether the two polymorphic forms Type I and II of N-4-carboxyphenyl-3-(6-oxohydropurin-9-yl) propanamide monopotassium salt show a varying solubility behavior in aqueous solutions.

Under controlled conditions of the manufacturing (e.g. hydrolysis of the N-4-carboxyphenyl-3-(6-oxohydropurin-9-yl) propanamide ethyl ester, drying process) only one single consistent Type I crystal structure with a characteristic powder pattern is obtained. Incubation of N-4-carboxyphenyl-3-(6-oxohydropurin-9-yl) propanamide monopotassium salt Type I and II at 70° C. with water vapor does not significantly alter the water content of either sample. Results from the interconversion studies demonstrated that the manufacturing process for N-4-carboxyphenyl-3-(6-oxohydropurin-9-yl) propanamide monopotassium salt monohydrate results in a product with a uniformly stable crystal structure.

Solubility

Figure 2:
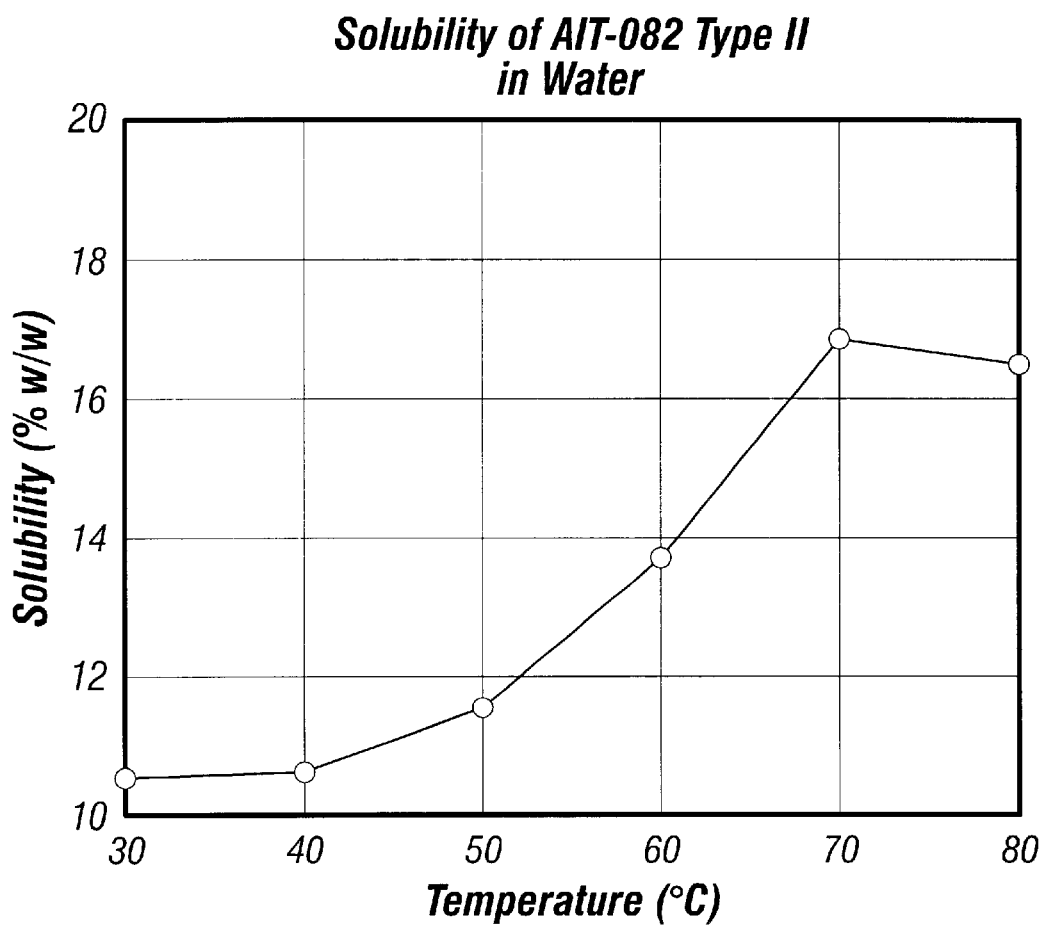
FIG. 2 is a graph showing the solubility of the Type II form of N-4-carboxyphenyl-3-(6-oxohydropurin-9-yl) propanamide monopotassium salt as a function of increasing temperature.

N-4-carboxyphenyl-3-(6-oxohydropurin-9-yl) propanamide monopotassium salt monohydrate Type I exhibits a good solubility in water (5% (w/v) at 25° C.). In aqueous solutions prepared with material which was synthesized by the route designated "direct crystallization" a fine microcrystalline precipitate of the N-4-carboxyphenyl-3-(6-oxohydropurin-9-yl) propanamide free acid was formed after 2–3 min. Although the assay of K is 1.0 equivalent and although direct crystallized K-salt is isolated at equal or slightly higher pH (H 8.7) than K-salt synthesized from N-4-carboxyphenyl-3-(6-oxohydropurin-9-yl) propanamide free acid (pH 8.5), only the latter is completely soluble in water. The precipitation of the free acid form can be explained by the occurrence of an equilibrium between the mono-K-salt and the di-K-salt of N-4-carboxyphenyl-3-(6-oxohydropurin-9-yl) propanamide free acid (2 mono-K-salt⇌di-K-salt+free acid) and the extreme low solubility of the free acid in water. The free acid precipitates and generates the di-K salt until its concentration is high enough to keep the precipitation and dissolution of the free acid at equilibrium. The solubility of N-4-carboxyphenyl-3-(6-oxohydropurin-9-yl) propanamide Type II (lot Am 960/a) in aqueous solution was measured as a function of temperature (FIG. 2). In the solubility curve a plateau is reached at 70° C. (17% w/w).

Further characterization of the Type III crystalline form was done as described above for Types I and II. The X-ray diffraction powder pattern of Type III is shown in FIG. 7(a); FIG. 7(b) shows the X-ray diffraction powder pattern of Type I for comparison.

Figure 8:
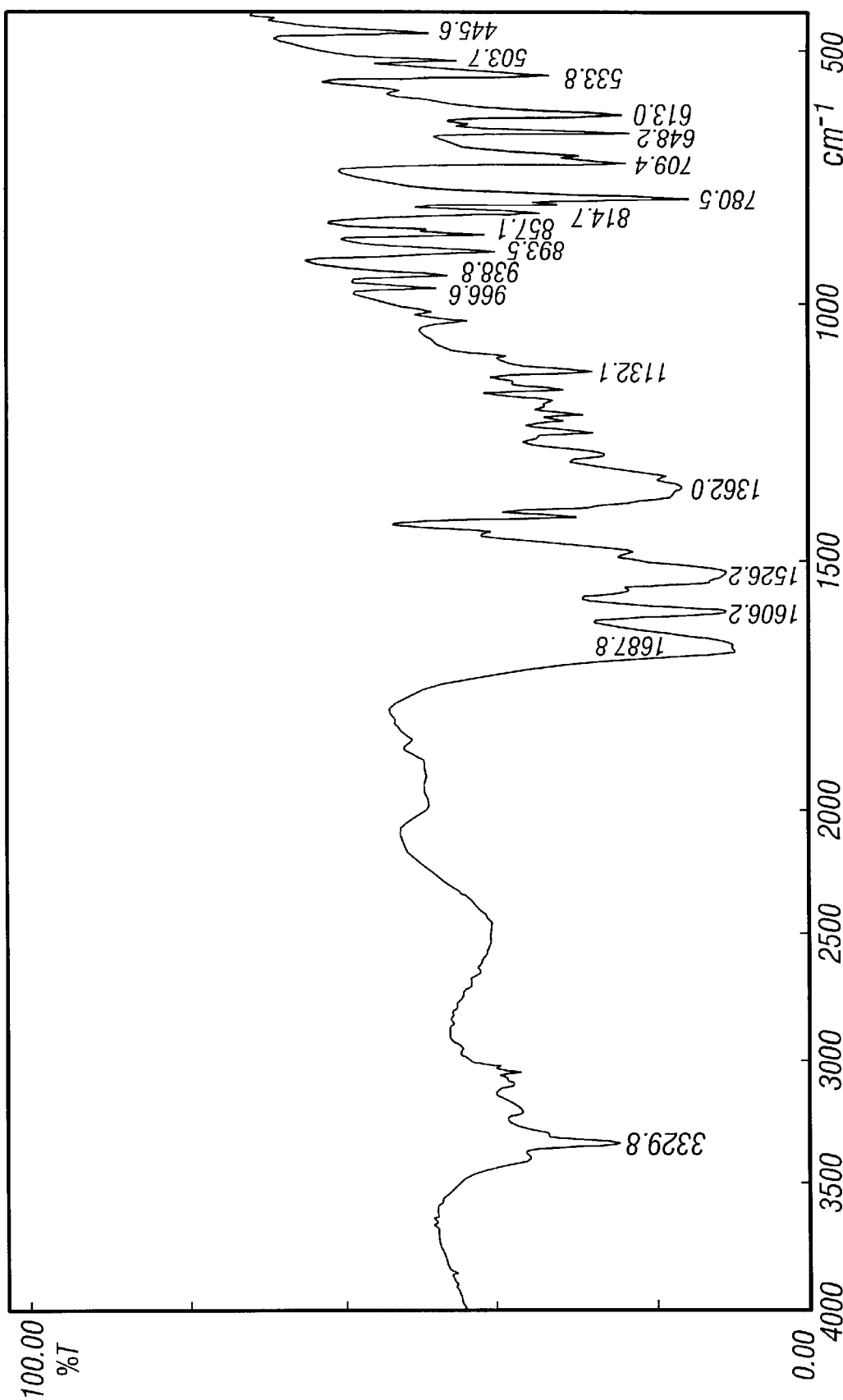
FIG. 8 shows the Fourier-transform infrared spectrum of the Type III crystal form of N-4-carboxyphenyl-3-(6-oxohydropurin-9-yl) propanamide (sample designated NTA-107-B/a)

The Fourier-transform infrared spectrum of the Type III crystal structure is shown in FIG. 8. The peak of the infrared spectrum is at 1687.8 $cm^{-1}$.

Figure 9:
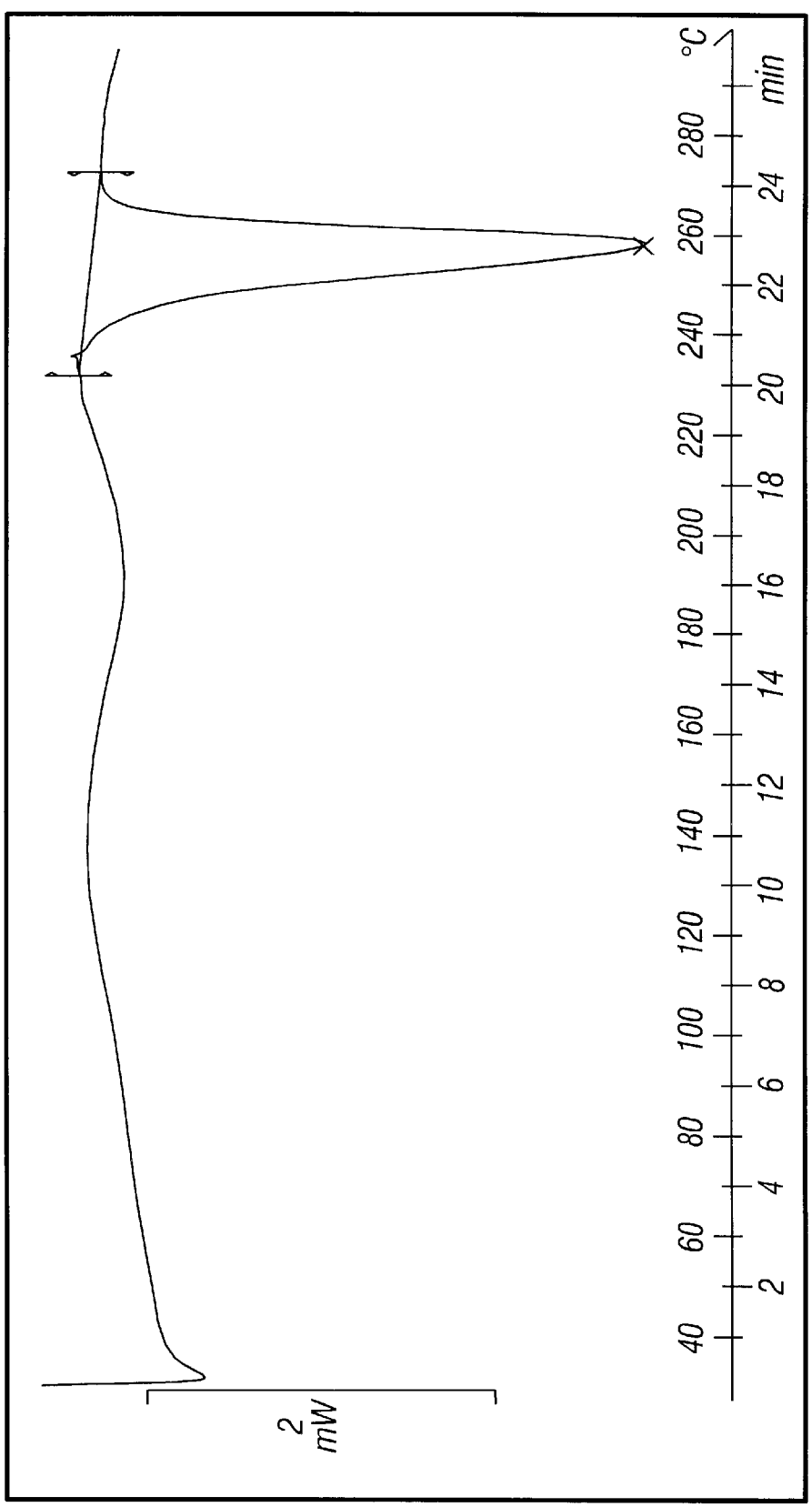
FIG. 9 shows the DSC measurement on the Type III crystal form of N-4-carboxyphenyl-3-(6-oxohydropurin-9-yl) propanamide (sample designated NTA-107-B/a)

The DSC plot of the Type III crystal form is shown in FIG. 9.

Figure 10:
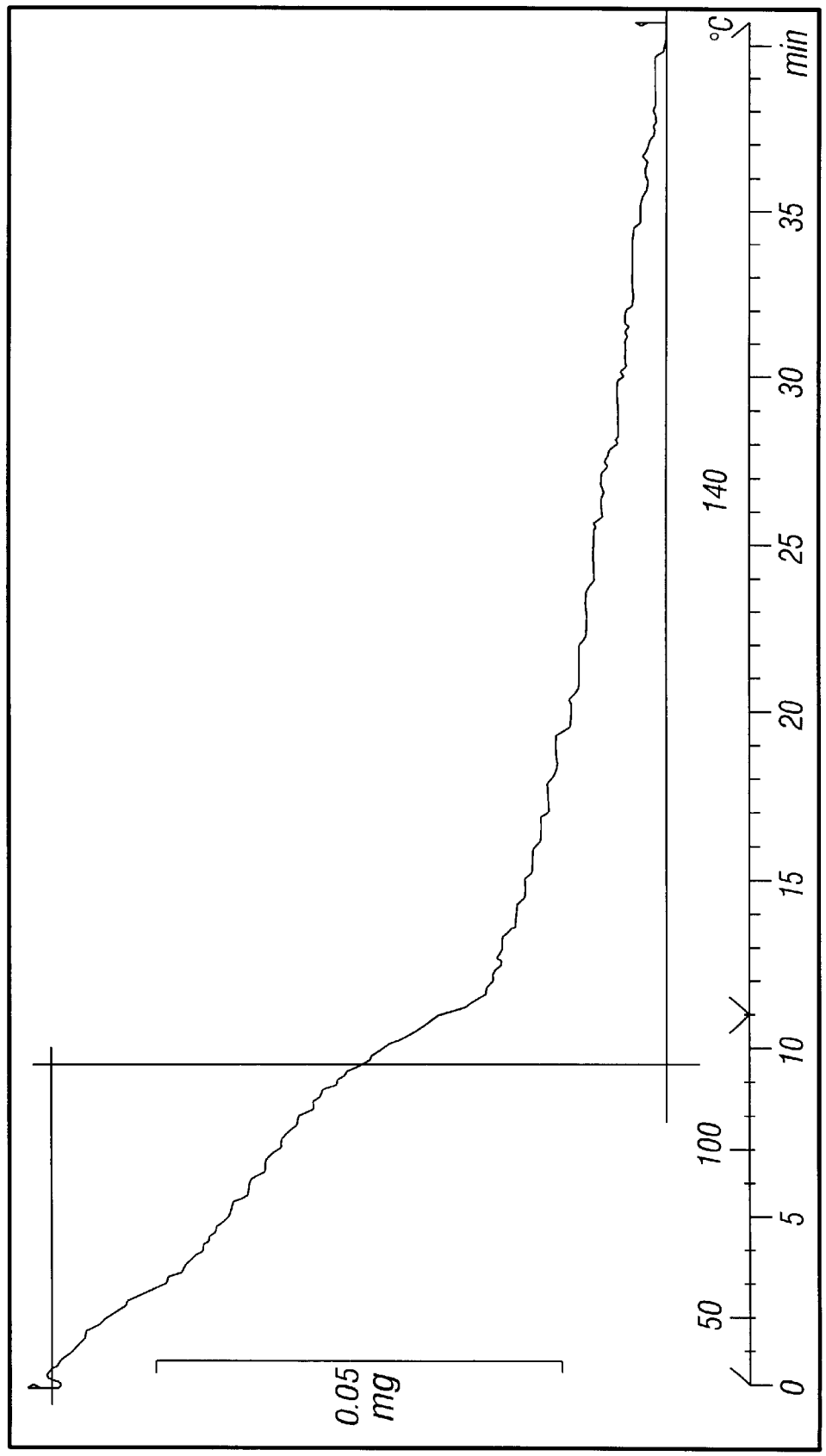
FIG. 10 shows the TG measurement on the Type III crystal form of N-4-carboxyphenyl-3-(6-oxohydropurin-9-yl) propanamide (sample designated NTA-107-B/a).

The TG plot of the Type III crystal form is shown in FIG. 10. Analysis of the data of FIG. 10 yields a figure of 0.91% for the amount of water present, in close agreement with the value of 0.87% obtained for the Type III crystal structure by Karl Fischer titration.

Conclusion

The occurrence of different crystalline forms of N-4-carboxyphenyl-3-(6-oxohydropurin-9-yl) propanamide monopotassium salt (polymorphism) can be attributed to the different crystal water content of the substance (Table 1). The different crystal structures, designated Type I, II and III, can be easily identified by their characteristic X-ray powder patterns which are of good quality. Powder diagrams of different batches of N-4-carboxyphenyl-3-(6-oxohydropurin-9-yl) propanamide monopotassium salt monohydrate of Type I show uniform patterns in terms of peak position and intensity. Interconversions of the crystal structures can be achieved by drying or humidification. The fully hydrated crystal structure of Type I containing one crystal water is not susceptible to small changes in total water content (bound crystal water and "adherent" water) with regard to its powder pattern.

TABLE 1

AIT-082 crystal structures

| Structure | Batch No. | KF | TG | X-ray no. (FIG. 3) | FT-IR | DSC |
|---|---|---|---|---|---|---|
| Type I | NTA-107-B | 5.77% | 1.94% | γ-97105 | 1674.1 cm$^{-1}$ | crystal water |
| Type I | DD-477-21-5 | 5.36% | 1.92% | γ-97081 | 1675.7 cm$^{-1}$ | crystal water |
| Type I & K$_2$-salt | Am 964/b | 7.04% | 2.96% | γ-97090 | 1674.4 cm$^{-1}$ | n.a. |
| Type II | NTA-107-A | 10.05% | 11.69% | γ-97106 | 1693.4 cm$^{-1}$ | adherent water |
| Type III | NTA-107-B/2 | 0.85% | 0.91% | γ-97112 | 1687.8 cm$^{-1}$ | crystal water |

TABLE 2

AIT-082 Interconversions

| FIG. 1 No. | Interconverison | Batch No. | X-ray No. (FIG. 3) | FT-IR |
|---|---|---|---|---|
| 1 | Type II→ | Am 927/a | γ-97080 | 1690.6 cm$^{-1}$ |
| 25° C., H$_2$O, vap. | Type II | Am 927/a RT | γ-97084 | n.a. |
| 2 | Type II→ | Am 927/a | γ-97080 | 1690.6 cm$^{-1}$ |
| 70° C., H$_2$O, vap. | Type I | Am 927/a 70° C. | γ-97085 | n.a. |
| 3 | Type I→ | DD-477-21-5 | γ-97080 | 1675.7 cm$^{-1}$ |
| 25° C., H$_2$O, vap. | Type I | DD-477-21-5 RT | γ-97084 | n.a. |
| 4 | Type I | DD-477-21-5 | γ-97080 | 1675.7 cm$^{-1}$ |
| 70° C., H$_2$O, vap. | Type I | DD-477-21-5 70° C. | γ-97085 | n.a. |
| 5 | Type I | NTA-107-B | γ-97112 | 1674.1 cm$^{-1}$ |
| 140° C., 5 mbar | Type III | NTA-107-B/2 | γ-97112 | n.a. |
| 25° C., H$_2$O vap. | Type III | NTA-107-B/2 | γ-97112 | n.a. |
| | Type I | NTA-107-B/3 | γ-97112 | n.a. | n.a. = not available

ADVANTAGES OF THE INVENTION

The synthetic methods of the present invention provide an efficient and economical method of synthesizing 9-substituted hypoxanthine derivatives, particularly N-4-carboxyphenyl-3-(6-oxohydropurin-9-yl) propanamide monopotassium salt, in a crystalline form that provides high stability and purity along with pharmaceutical acceptability. These methods use available starting materials, require a minimum number of steps, and provide a product of high purity and bioavailability and consistent crystal structure with a minimum of purification. Methods were developed to synthesize different crystal types of the final product and to transform them into the most stable type. The procedure avoids side reactions that complicate isolation and purification of the final product.

Although the present invention has been described in considerable detail, with reference to certain preferred versions thereof, other versions and embodiments are possible. Therefore, the scope of the invention is determined by the following claims.

We claim:

1. A method for synthesizing a crystalline form of the monopotassium salt of N-4-carboxyphenyl-3-(6-oxohydropurin-9-yl) propanamide monohydrate that has a solubility of about 5% (w/v) in water at 25° C. and has an infrared spectrum peak from about 1674.1 cm$^{-1}$ to about 1675.7 cm$^{-1}$ as measured by Fourier-transform infrared spectroscopy in the absence of a medium, the crystalline form being designated Type I, comprising the steps of:

(a) reacting the free acid of N-4-carboxyphenyl-3-(6-oxohydropurin-9-yl) propanamide with potassium hydroxide in water; and (b) precipitating the product of step (a) with ethanol to yield the Type I crystalline form of the monopotassium salt of N-4-carboxyphenyl-3-(6-oxohydropurin-9-yl) propanamide.

2. A method for converting a distinct crystalline form of the monopotassium salt of N-4-carboxyphenyl-3-(6-oxohydropurin-9-yl) propanamide, designated Type II, to a crystalline form of the monopotassium salt of N-4-carboxyphenyl-3-(6-oxohydropurin-9-yl) propanamide monohydrate having a solubility of about 5% (w/v) in water at 25° C. and an infrared spectrum peak from about 1674.1 cm$^{-1}$ to about 1675.7 cm$^{-1}$ as measured by Fourier-transform infrared spectroscopy in the absence of a medium, designated Type I, comprising the step of equilibrating the crystalline form of the monopotassium salt of N-4-carboxyphenyl-3-(6-oxohydropurin-9-yl) propanamide designated Type II with water vapor at a temperature in a range from about 60° C. to about 80° C. for a time period of from about 36 hours to about 60 hours to yield the crystalline form of the monopotassium salt of N-4-carboxyphenyl-3-(6-oxohydropurin-9-yl) propanamide monohydrate designated Type I.

3. The method of claim 2 wherein the temperature is about 70° C.

4. The method of claim 2 wherein the time period is about 48 hours.

5. The method of claim 3 wherein the time period is about 48 hours.

6. A method for converting a distinct crystalline form of the monopotassium salt of N-4-carboxyphenyl-3-(6-oxohydropurin-9-yl) propanamide, designated Type III, to a crystalline form of the monopotassium salt of N-4-carboxyphenyl-3-(6-oxohydropurin-9-yl) propanamide monohydrate that has a solubility of about 5% in water and that has an infrared spectrum peak from about 1674.1 cm$^{-1}$ to about 1675.7 cm$^{-1}$ as measured by Fourier-transform infrared spectroscopy in the absence of a medium, designated Type I, comprising the step of equilibrating the crystalline form of the monopotassium salt of N-4-carboxyphenyl-3-(6-oxohydropurin-9-yl) propanamide designated Type III with water vapor at about 25° C. to yield the crystalline form of the monopotassium salt of N-4-carboxyphenyl-3-(6-oxohydropurin-9-yl) propanamide monohydrate designated Type I.

* * * * *